US011478662B2

(12) United States Patent
Sayeh et al.

(10) Patent No.: US 11,478,662 B2
(45) Date of Patent: Oct. 25, 2022

(54) SEQUENTIAL MONOSCOPIC TRACKING

(71) Applicant: Accuray Incorporated, Sunnyvale, CA (US)

(72) Inventors: Sohail Sayeh, San Ramon, CA (US); Eric Schnarr, McFarland, WI (US); Petr Jordan, Redwood City, CA (US); Calvin R. Maurer, Jr., San Jose, CA (US); Jay B. West, Mountain View, CA (US); Robert O'Connell, Madison, WI (US)

(73) Assignee: Accuray Incorporated, Sunnyvale, CA (US)

( * ) Notice: Subject to any disclaimer, the term of this patent is extended or adjusted under 35 U.S.C. 154(b) by 294 days.

(21) Appl. No.: 15/945,580

(22) Filed: Apr. 4, 2018

(65) Prior Publication Data

US 2018/0289982 A1 Oct. 11, 2018

Related U.S. Application Data

(60) Provisional application No. 62/482,604, filed on Apr. 6, 2017, provisional application No. 62/482,135, filed on Apr. 5, 2017.

(51) Int. Cl.
*A61N 5/10* (2006.01)
*G06T 7/73* (2017.01)
(Continued)

(52) U.S. Cl.
CPC .......... *A61N 5/1049* (2013.01); *A61B 6/5264* (2013.01); *A61B 90/39* (2016.02);
(Continued)

(58) Field of Classification Search
CPC ..... A61B 90/39; A61B 6/5264; A61B 6/0457; A61B 6/4014; A61B 2034/2046;
(Continued)

(56) References Cited

U.S. PATENT DOCUMENTS 4,132,896 A 1/1979 Klotz et al.
4,237,901 A 12/1980 Taenzer
(Continued)

FOREIGN PATENT DOCUMENTS

EP 1004272 A1 5/2000
JP 05188199 A 7/1993
(Continued)

OTHER PUBLICATIONS

Brain Waves "Dynamic IMRS Intensity Modulated Radiosurgery", BrainLAB AG, Summer 2000; 8 pages.
(Continued)

*Primary Examiner* — Joseph M Santos Rodriguez
*Assistant Examiner* — Kaitlyn E Sebastian
(74) *Attorney, Agent, or Firm* — Womble Bond Dickinson (US) LLP

(57) ABSTRACT

A method of sequential monoscopic tracking is described. The method includes generating a plurality of projections of an internal target region within a body of a patient, the plurality of projections comprising projection data about a position of an internal target region of the patient. The method further includes generating external positional data about external motion of the body of the patient using one or more external sensors. The method further includes generating, by a processing device, a correlation model between the projection data and the external positional data by fitting the plurality of projections of the internal target region to the external positional data. The method further includes estimating the position of the internal target region at a later time using the correlation model.

27 Claims, 13 Drawing Sheets

(51) Int. Cl.

| | | |
|---|---|---|
| *G06T 7/00* | (2017.01) | |
| *A61B 6/00* | (2006.01) | |
| *A61B 6/03* | (2006.01) | |
| *A61B 90/00* | (2016.01) | |
| *G16H 20/40* | (2018.01) | |
| *G16H 40/63* | (2018.01) | |
| *G16H 30/40* | (2018.01) | |
| *G06T 7/33* | (2017.01) | |
| *A61B 34/20* | (2016.01) | |
| *A61B 6/12* | (2006.01) | |
| *A61B 6/04* | (2006.01) | |

(52) U.S. Cl.
CPC ............ *A61N 5/107* (2013.01); *A61N 5/1067* (2013.01); *G06T 7/33* (2017.01); *G06T 7/73* (2017.01); *G06T 7/75* (2017.01); *G06T 7/97* (2017.01); *G16H 20/40* (2018.01); *G16H 30/40* (2018.01); *G16H 40/63* (2018.01); *A61B 6/032* (2013.01); *A61B 6/0487* (2020.08); *A61B 6/12* (2013.01); *A61B 6/4014* (2013.01); *A61B 6/4085* (2013.01); *A61B 6/4441* (2013.01); *A61B 2034/2046* (2016.02); *A61B 2034/2055* (2016.02); *A61B 2034/2065* (2016.02); *A61B 2090/367* (2016.02); *A61B 2090/3983* (2016.02); *A61N 2005/1051* (2013.01); *A61N 2005/1061* (2013.01); *A61N 2005/1091* (2013.01); *G06T 2207/10024* (2013.01); *G06T 2207/10081* (2013.01); *G06T 2207/10116* (2013.01); *G06T 2207/30004* (2013.01); *G06T 2207/30204* (2013.01)

(58) Field of Classification Search
CPC ......... A61B 6/4441; A61B 6/12; A61B 6/032; A61B 6/4085; A61B 6/4435; A61B 2090/367; A61B 2034/2065; A61B 2034/2055; A61B 2090/3983; A61N 5/1049; A61N 5/1067; A61N 5/107; A61N 2005/1061; A61N 2005/1051; A61N 5/1068; A61N 2005/1091; G16H 20/40; G16H 40/63; G16H 30/40; G06T 7/73; G06T 7/33; G06T 7/75; G06T 7/97; G06T 2207/10024; G06T 2207/30004; G06T 2207/10081; G06T 2207/10116; G06T 2207/30204

See application file for complete search history.

(56) References Cited

U.S. PATENT DOCUMENTS

| | | |
|---|---|---|
| 4,249,106 A | 2/1981 | Maruyama et al. |
| 4,583,538 A | 4/1986 | Onik et al. |
| 4,791,934 A | 12/1988 | Brunnett |
| 5,067,981 A | 11/1991 | Hooykaas |
| 5,207,223 A | 5/1993 | Adler |
| 5,222,499 A | 6/1993 | Allen et al. |
| 5,278,886 A | 1/1994 | Kobiki et al. |
| 5,394,875 A | 3/1995 | Lewis et al. |
| 5,397,329 A | 3/1995 | Allen |
| 5,411,026 A | 5/1995 | Carol |
| 5,427,097 A | 6/1995 | Depp |
| 5,430,308 A | 7/1995 | Feichtner et al. |
| 5,446,548 A | 8/1995 | Gerig et al. |
| 5,447,154 A | 9/1995 | Cinquin et al. |
| 5,537,452 A | 7/1996 | Shepherd et al. |
| 5,538,494 A | 7/1996 | Matsuda |
| 5,588,430 A | 12/1996 | Bova et al. |
| 5,622,187 A | 4/1997 | Carol |
| 5,628,315 A | 5/1997 | Vilsmeier et al. |
| 5,727,554 A | 3/1998 | Kalend et al. |
| 5,748,700 A | 5/1998 | Shepherd et al. |
| 5,764,723 A | 6/1998 | Weinberger et al. |
| 5,769,861 A | 6/1998 | Vilsmeier |
| 5,784,431 A | 7/1998 | Kalend et al. |
| 5,797,849 A | 8/1998 | Vesely et al. |
| 5,943,719 A | 8/1999 | Feldman et al. |
| 5,967,981 A | 10/1999 | Watrous |
| 5,971,997 A | 10/1999 | Guthrie et al. |
| 6,006,126 A | 12/1999 | Cosman |
| 6,019,724 A | 2/2000 | Gronningsaeter et al. |
| 6,031,888 A | 2/2000 | Ivan et al. |
| 6,076,005 A | 6/2000 | Sontag et al. |
| 6,110,112 A | 8/2000 | Heywang-Koebrunner |
| 6,120,453 A | 9/2000 | Sharp |
| 6,144,875 A | 11/2000 | Schweikard et al. |
| 6,149,592 A | 11/2000 | Yanof et al. |
| 6,219,403 B1 | 4/2001 | Nishihara |
| 6,246,898 B1 | 6/2001 | Vesely et al. |
| 6,256,372 B1 | 7/2001 | Aufrichtig et al. |
| 6,275,721 B1 | 8/2001 | Darrow et al. |
| 6,285,902 B1 | 9/2001 | Kienzle, III et al. |
| 6,301,495 B1 | 10/2001 | Gueziec et al. |
| 6,307,914 B1 | 10/2001 | Kunieda et al. |
| 6,314,312 B1 | 11/2001 | Wessels et al. |
| 6,325,758 B1 | 12/2001 | Carol et al. |
| 6,380,958 B1 | 4/2002 | Guendel et al. |
| 6,405,072 B1 | 6/2002 | Cosman |
| 6,470,207 B1 | 10/2002 | Simon et al. |
| 6,473,634 B1 | 10/2002 | Barni |
| 6,501,981 B1 | 12/2002 | Schweikard et al. |
| 6,681,129 B2 | 1/2004 | Matsuzaki et al. |
| 6,690,965 B1 | 2/2004 | Riaziat et al. |
| 6,778,850 B1 | 8/2004 | Adler et al. |
| 7,318,805 B2 | 1/2008 | Schweikard et al. |
| 8,634,898 B2 | 1/2014 | Adler et al. |
| 2002/0032453 A1 | 3/2002 | Cosman |
| 2002/0065461 A1 | 5/2002 | Cosman |
| 2002/0154728 A1 | 10/2002 | Morita et al. |
| 2008/0130825 A1* | 6/2008 | Fu ............................ G06T 7/248 378/8 |
| 2009/0180678 A1* | 7/2009 | Kuduvalli ............ A61N 5/1049 382/132 |
| 2011/0301449 A1* | 12/2011 | Maurer, Jr. ............ A61B 6/032 600/411 |
| 2012/0008734 A1* | 1/2012 | Thomson ............ A61B 6/4085 378/4 |
| 2012/0078090 A1* | 3/2012 | Adler ..................... A61B 90/10 600/427 |
| 2012/0106704 A1* | 5/2012 | Maurer, Jr ............ A61N 5/1037 378/65 |
| 2015/0243025 A1* | 8/2015 | Berlinger ................ A61B 6/486 382/131 |
| 2017/0368369 A1* | 12/2017 | Heinrich .................. G06T 7/251 |

FOREIGN PATENT DOCUMENTS

| | | |
|---|---|---|
| JP | 6502330 A | 3/1994 |
| JP | 06181918 A | 7/1994 |
| JP | 8112272 A | 5/1996 |
| JP | 10201863 A | 8/1998 |
| JP | 1119082 A | 1/1999 |
| JP | 2000201922 A | 7/2000 |
| JP | 2000217810 A | 8/2000 |
| JP | 2000237335 A | 9/2000 |
| JP | 2003523220 A | 8/2003 |
| JP | 2013544137 A | 12/2013 |
| WO | 9740766 A1 | 11/1997 |
| WO | 0007669 A1 | 2/2000 |
| WO | 0054689 A1 | 9/2000 |
| WO | 2011156526 A2 | 12/2011 |
| WO | 2012058615 A1 | 5/2012 |
| WO | 2017093034 A1 | 6/2017 |

OTHER PUBLICATIONS

Brain Waves "Novalis Body", BrainLAB AG, Summer 2001; 8 pages.

(56) References Cited

OTHER PUBLICATIONS

Schnarr et al. "Feasability of real-time motion management with helical tomotherapy", Accuray Incorporated study, 26 pages.
English Abstract JP8112272 published May 7, 1996, 1 page.
Examination Report for Japanese Patent Application 2002-526277, dated Sep. 22, 2006, 3 pages.
Examination Report for Japanese Patent Application 2002-526277, dated May 18, 2006, 4 pages.
Examination Report for Japanese Patent Application 2002-526277, dated Apr. 19, 2007, 4 pages.
Examination Report for European Patent Application No. 01 970 945.0, dated Feb. 23, 2010, 6 pages.
Examination Report for European Patent Application No. 01 970 945.0, dated Jan. 16, 2007, 7 pages.
Supplementary European Search Report for European Patent Application No. 01 970 945.0 dated Apr. 5, 2006, 5 pages.
Supplementary European Search Report for European Patent Application No. 01 970 945.0 dated Oct. 16, 2006, 5 pages.
Supplementary Partial European Search Report, Application No. EP01970945, dated Jun. 28, 2006.
Coste-Maniere, E., (2005). "Robotic Whole Body Stereotactic Radiosurgery: Clinical Advantages of the CyberKnife® Integrated System," The International ournal of Medical Robotics + Computer Assisted Surgery, www.roboticpublications.com, pp. 28-39.
Minohara, S. et al. (Jul. 2000). "Respiratory Gated Irridation System for Heavy-Ion Radiotherapy," International Journal of Radiation: Oncology Biology Physics, Pergamon Press, US vol. 47, No. 4, ISSN-0360-3016.
Japanese Office Action and Search Report on the Patentability of Application No. 2019-554795 dated Dec. 1, 2021, 14 pages.
Int'l Search Report and Written Opinion of the ISA/EP in PCT/US2018/026323 dated Jul. 5, 2018; 13 pgs.

\* cited by examiner

SEQUENTIAL MONOSCOPIC TRACKING

CROSS-REFERENCE TO RELATED APPLICATIONS

This application claims the benefit of U.S. Provisional Patent Application No. 62/482,135, filed Apr. 5, 2017 and of U.S. Provisional Patent Application No. 62/482,604, filed Apr. 6, 2017, the entire contents of both of which are hereby incorporated by reference.

TECHNICAL FIELD

Embodiments of the present disclosure relate to tracking a position of a target using data from x-ray imagers.

BACKGROUND

In radiation treatment, doses of radiation delivered via a radiation treatment beam from a source outside a patient's body are delivered to a target region in the body, in order to destroy tumorous cells. Typically, the target region consists of a volume of tumorous tissue. During radiation treatment, care must be taken to track movement of the target region, so that treatment doses of the radiation treatment beam are directed to the intended area of the patient's body.

BRIEF DESCRIPTION OF THE DRAWINGS

Embodiments of the present disclosure are illustrated by way of example, and not by way of limitation, in the figures of the accompanying drawings.

DETAILED DESCRIPTION

Described herein are embodiments of methods and apparatus for sequential monoscopic tracking. Embodiments of the present disclosure may be used with a radiation treatment delivery system such as the CyberKnife® radiosurgery system that includes stereo x-ray imaging capability. Alternatively, other types of radiation treatment delivery systems (e.g., gantry based, helical based, etc.) may be used.

In one embodiment, a radiation treatment system includes a linear accelerator (LINAC) 1201 that acts as a radiation treatment source. It is important to ensure that during treatment, any movement of a target region of patient is carefully tracked so that doses of radiation treatment are directed to the intended target. A sequential monoscopic tracking system, such as that described herein, would therefore be desirable in radiation treatment systems such as the CyberKnife® radiation treatment system.

Figure 1A:
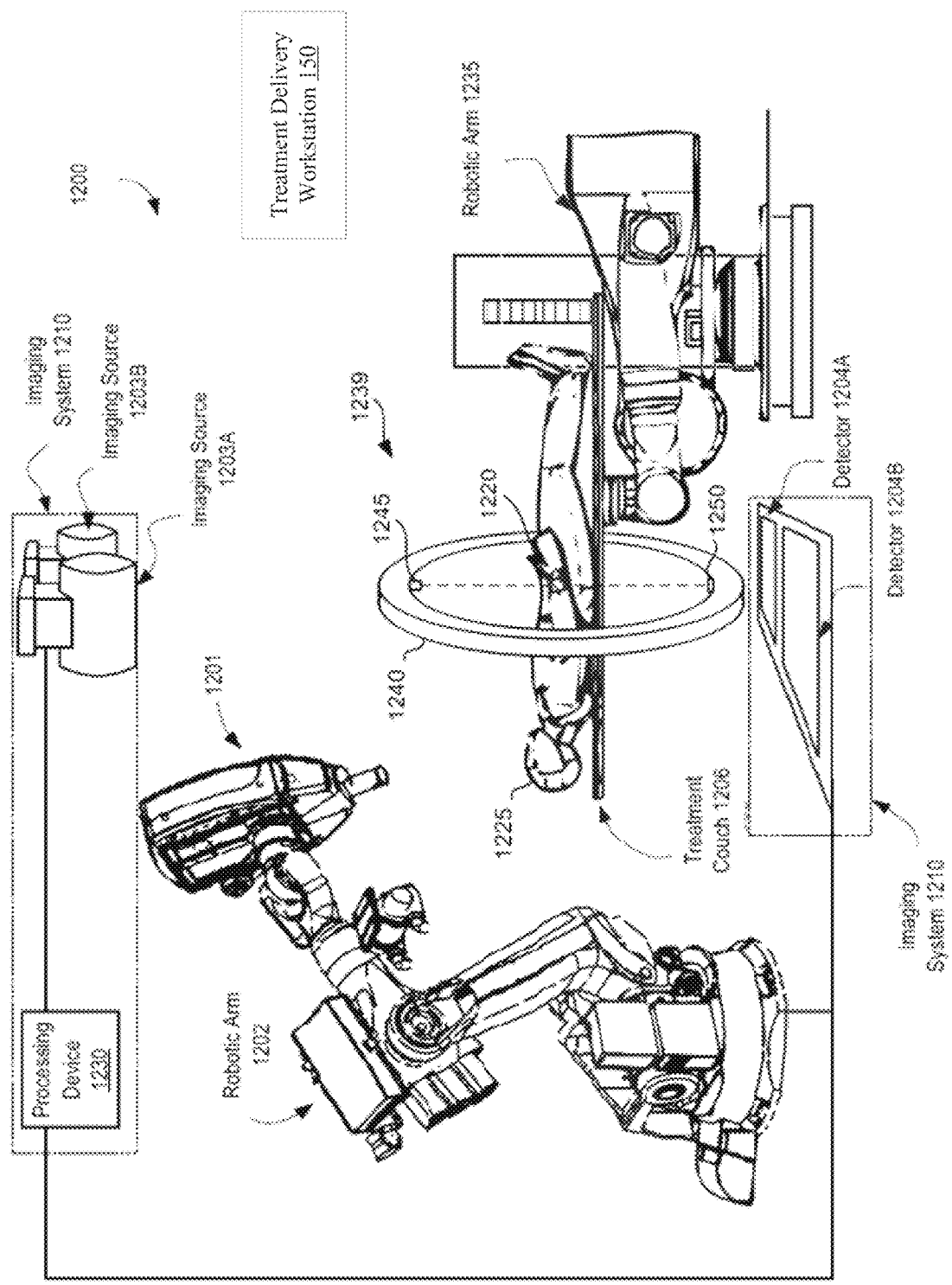
FIG. 1A illustrates a radiation treatment system that may be used in accordance with embodiments described herein.

The use of a volumetric imaging system (e.g., the medPhoton ImagingRing System (IRS)) with a radiation treatment delivery system (e.g., the CyberKnife® radiation treatment system) as shown in FIG. 1A enables new image registration and image tracking opportunities. For example, in embodiments of the present disclosure, such systems may acquire two or more flat-panel X-ray images using only a single imager.

Embodiments of the present disclosure track the 3D position of a target inside a patient using data from x-ray images acquired sequentially from two or more flat-panel X-ray images acquired at different times. Such imaging may be referred to as sequential monoscopic imaging because single (monoscopic) images are taken sequentially (e.g., several seconds apart) from different angles. In some embodiments, images may be taken between once every second to once every minute, inclusive. In other embodiments, images may be taken between once every 100 milliseconds to once every two minutes, inclusive. A distinction from the stereo x-ray imaging is that a single monoscopic image does not fully define the position of the target in 3D space. An object visualized in a single x-ray image lies somewhere on a line that connects the x-ray source and the position of the object in the x-ray image.

Information about the object position from a sequence of individual images acquired from different positions may be fitted to a correlation model simultaneously to estimate the most likely trajectory of the target over the observed period. The correlation between a moving 3D target position and an externally detected breathing amplitude may be modeled using projections acquired from multiple individual flat-panel X-ray images (e.g., monoscopic projection images), all acquired at different times and from at least two different positions. Using the mathematical formulae described herein, the monoscopic projection images may be fitted to a 3D model to estimate the trajectory of the target over a period of time In one embodiment, a projection (also referred to herein as a "projection image") may be an image depicting the internal region in a body projected to a plane (2D) outside the body from a single viewing angle. In this embodiment, an X-ray point source and a flat panel detector on opposite sides of the body may be used to acquire a projection image. The X-ray source and detector may be mounted on a ring gantry that rotates around the body, allowing projection images to be acquired from a variety of imaging angles.

In another embodiment, projection data may include both the lines between the 2D detector positions of the internal target and the x-ray point source, and/or the 2D detector positions themselves. In one embodiment, a correlation model between the 3D target position and the external sensor position may be fit by minimizing the distance between the model projected to the detector and the 2D detector positions, and/or by minimizing the distance between the model and the lines between the 2D detector positions and the x-ray point source.

For example, a correlation model may be generated by fitting the 2D target positions acquired at multiple time points to simultaneously acquired external measurements (e.g., external marker positions). Such a correlation model can be used for example in a radiation therapy system. In such a system, the correlation model can be generated before treatment; during treatment, the internal tumor position is estimated from the external measurements using the correlation model, and this information is used to move or shape the radiation beam dynamically with the target.

The term "target" may refer to one or more fiducials near (within some defined proximity to) a treatment area (e.g., a tumor). In another embodiment a target may be a bony structure. In yet another embodiment a target may refer to soft tissue (e.g., tumor) of a patient. A target may be any defined structure or area capable of being identified and tracked, as described herein.

FIG. 1A illustrates a radiation treatment system 1200 that may be used in accordance with embodiments described herein. As shown, FIG. 1A illustrates a configuration of a radiation treatment system 1200. In the illustrated embodiments, the radiation treatment system 1200 includes a linear accelerator (LINAC) 1201 that acts as a radiation treatment source. In one embodiment, the LINAC 1201 is mounted on the end of a robotic arm 1202 having multiple (e.g., 5 or more) degrees of freedom in order to position the LINAC 1201 to irradiate a pathological anatomy (e.g., target 1225) with beams delivered from many angles, in many planes, in an operating volume around a patient. Treatment may involve beam paths with a single isocenter, multiple isocenters, or with a non-isocentric approach. Alternatively, other types of image guided radiation treatment (IGRT) systems may be used. In one alternative embodiment, the LINAC 1201 may be mounted on a gantry based system as described below.

LINAC 1201 may be positioned at multiple different nodes (predefined positions at which the LINAC 1201 is stopped and radiation may be delivered) during treatment by moving the robotic arm 1235. At the nodes, the LINAC 1201 can deliver one or more radiation treatment beams to a target. The nodes may be arranged in an approximately spherical distribution about a patient. The particular number of nodes and the number of treatment beams applied at each node may vary as a function of the location and type of pathological anatomy to be treated.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 103A, 1203B and/or x-ray detectors 1204A, 1204B may be mobile, in which case they may be repositioned to maintain alignment with the target 120, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1A, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

In some embodiments, a gantry system with a helical delivery may be used to rotate the imaging system 1210. For example, the gantry system may be used to acquire two, three, or more images (e.g., x-ray images) at different angles. The radiation treatment delivery system may also include a rotational imaging system 1240 that is positioned around the patient.

In one implementation, the system 1200 includes a frameless robotic radiosurgery system (e.g., CyberKnife® treatment delivery system). In another implementation, the system 1200 is coupled to a gantry-based LINAC treatment system where, for example, LINAC 1201 is coupled to a gantry of a gantry based system. Alternatively, system 1200 may be used with other types of radiation treatment systems, for example, a helical delivery system as discussed below.

Figure 1B:
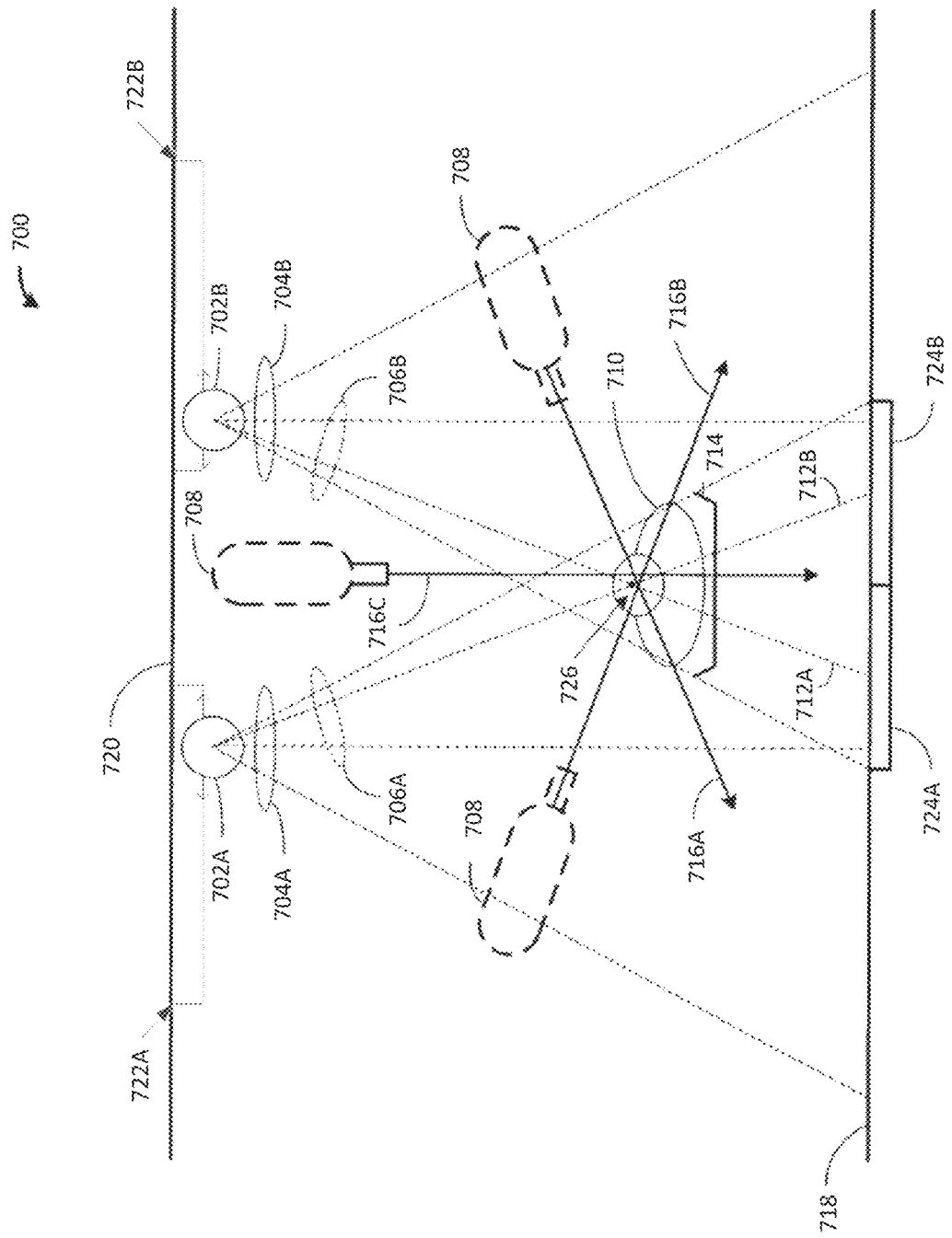
FIG. 1B is a cross-section of the radiation treatment system in accordance with embodiments described herein.

FIG. 1B illustrates the configuration of an image-guided radiation treatment (IGRT) system 700. In general, the IGRT system 700 may correspond to the radiation treatment system 1200 of FIG. 1A.

As shown in FIG. 1B, the IGRT system 700 may include two kilovoltage (kV) imaging sources 702A and 702B that may be mounted on tracks 722A and 722B on the ceiling 720 of an operating room and may be aligned to project imaging x-ray beams 704A, 704B, 706A, and 706B from two different positions such that a ray 712A of beam 704A intersects with a ray 712B of beam 704B at an imaging center 726 (i.e., isocenter), which provides a reference point for positioning the LINAC 708 to generate treatment beams 716A, 716B and 716C and the patient 710 on treatment couch 714 during treatment. After passing through the patient 710, imaging x-ray beams 704A and 704B may illuminate respective imaging surfaces of x-ray detectors 724A and 724B, which may be mounted at or near the floor 718 of the operating room and substantially parallel to each other (e.g., within 5 degrees). The kV imaging sources 702A and 702B may be substantially coplanar such that the imaging surfaces of kV imaging sources 702A and 702B form a single imaging plane. In one embodiment, kV imaging sources 702A and 702B may be replaced with a single kV imaging source. Once an x-ray image of the patient 710 has been generated, the LINAC 708 may rotate to generate a treatment beam 716 from a different angle. While the LINAC 708 rotates to the different angle, the kV imaging sources 702A and 702B may move along tracks 722A and 722B to generate x-ray images of the patient 710 from a new angle.

Figure 2A:
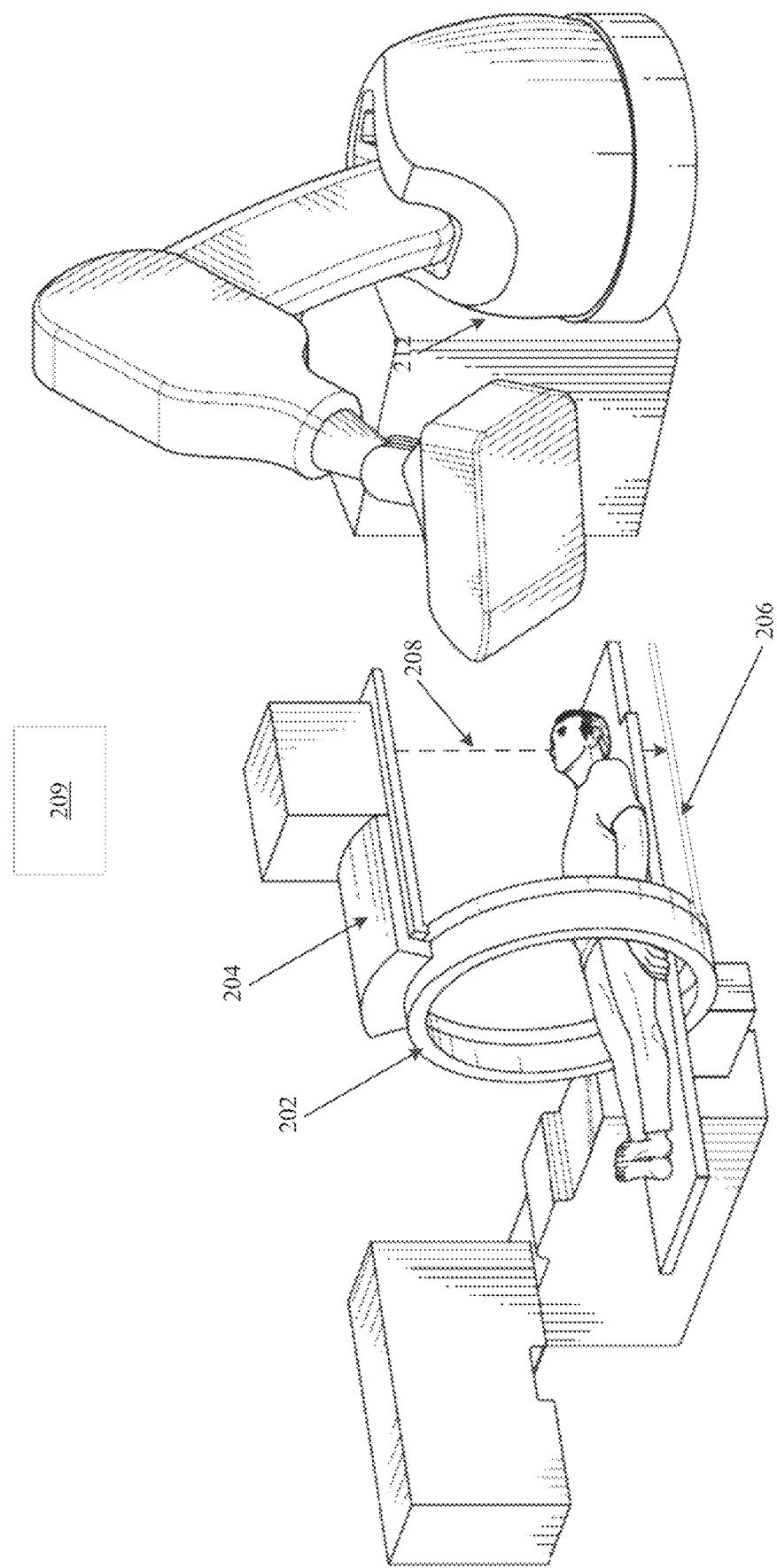
FIG. 2A illustrates a volumetric imaging device and a projection, in accordance with embodiments described herein.

FIG. 2A illustrates a volumetric imaging device 202 and a projection 208, in accordance with embodiments described herein. In one embodiment, the volumetric imaging device includes a source 204 and a detector 206. In one embodiment, the source 204 and detector 206 of the volumetric imager 202 may be used during radiation treatment to track a target and align a patient. In one embodiment, the volumetric imaging device 202 may be used to take a series of images, which may be used to perform the tracking and aligning. In another embodiment, the volumetric imaging device 202 may be used in combination with a second imager, such as a static 2D x-ray imager (e.g., 209), to perform the tracking and aligning. In one embodiment, a projection (e.g., a projection line) 208 is shown extending from the source 204 to the detector 206.

Figure 2B:
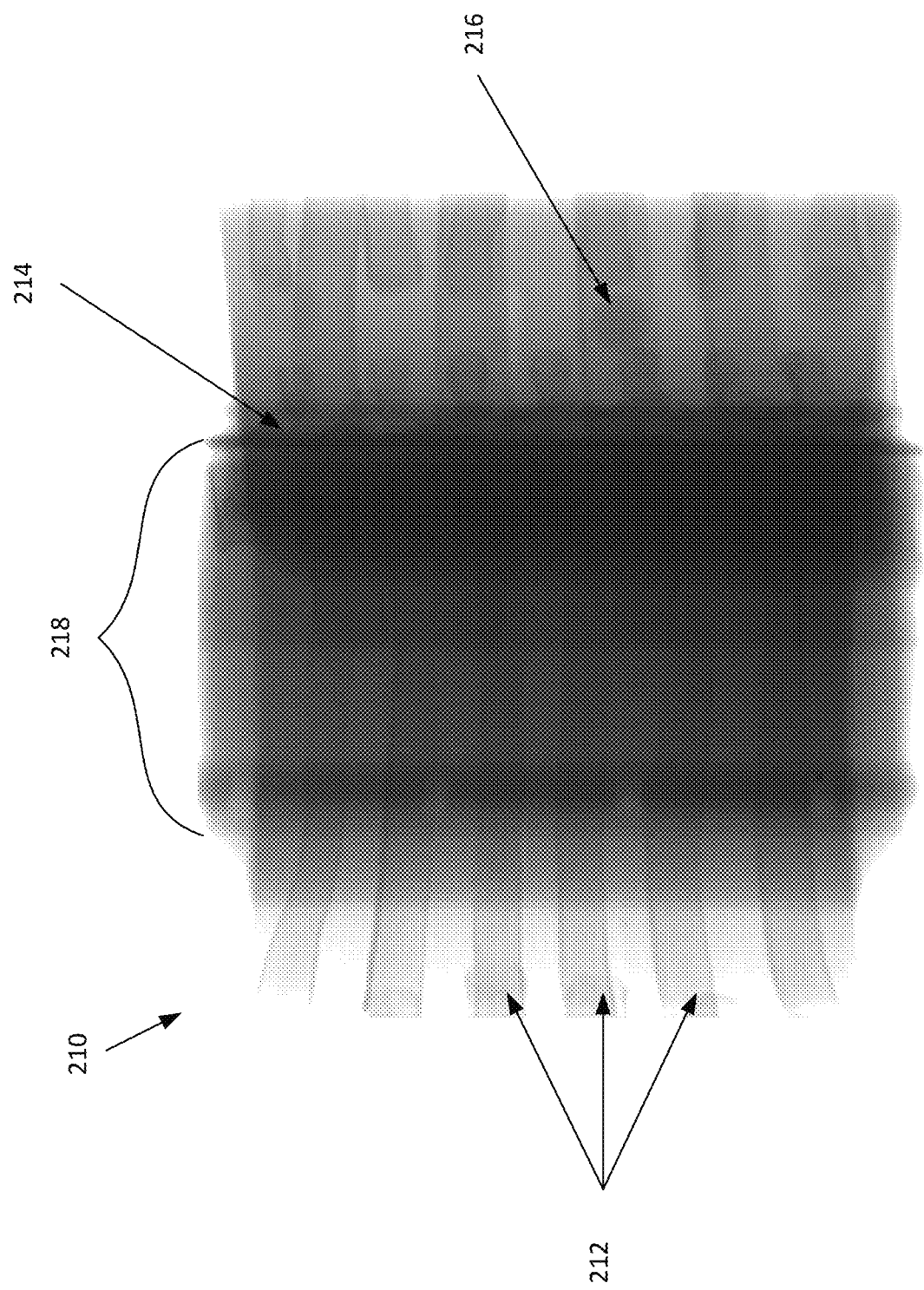
FIG. 2B illustrates a projection image, in accordance with embodiments described herein.

In one embodiment, projection data (e.g., from a projection image based on the projection line 208) may include both the lines 208 between the 2D detector 206 positions and the x-ray point source 204 and the 2D detector 206 positions themselves. Projection image 210 of FIG. 2B is one example of a projection image. The projection image 210 shows the 2D projection of simulated internal structures of a patient including ribs 212, a spine 214, mediastinum 218 (indicated by the dark region), and a lung tumor 216. In one embodiment, a correlation model may be fit by minimizing the distance between the model projected to the detector 206 and the 2D detector positions, and/or by minimizing the distance between the model and the lines 208 between the 2D detector 206 positions and the x-ray point source 204.

In one embodiment, a projection may be generated by any method of mapping 3D points to points in a 2D plane. For example, an x-ray point source 204 and a flat panel detector 206 may be mounted on the rotatable platform or gantry 202 on opposite sides of a body to acquire x-ray projection images of the body from various angles. Each image pixel has a scalar intensity value, which is approximately the integral of the linear attenuation coefficients encountered along the x-ray as it travels in a line 208 from the x-ray point source 204 to the detector 206. The x-ray imaging system projects 3D positions of internal body anatomy to 2D positions in the x-ray projection images. In this embodiment, internal positional data identifying a position of an internal target region of the patient may be 3D positions. As described herein, projections (or projection data) may refer to both the 2D positions in the x-ray projection images, and the lines 208 between the x-ray point source 204 and the 2D positions in the x-ray projection images.

Figure 3:
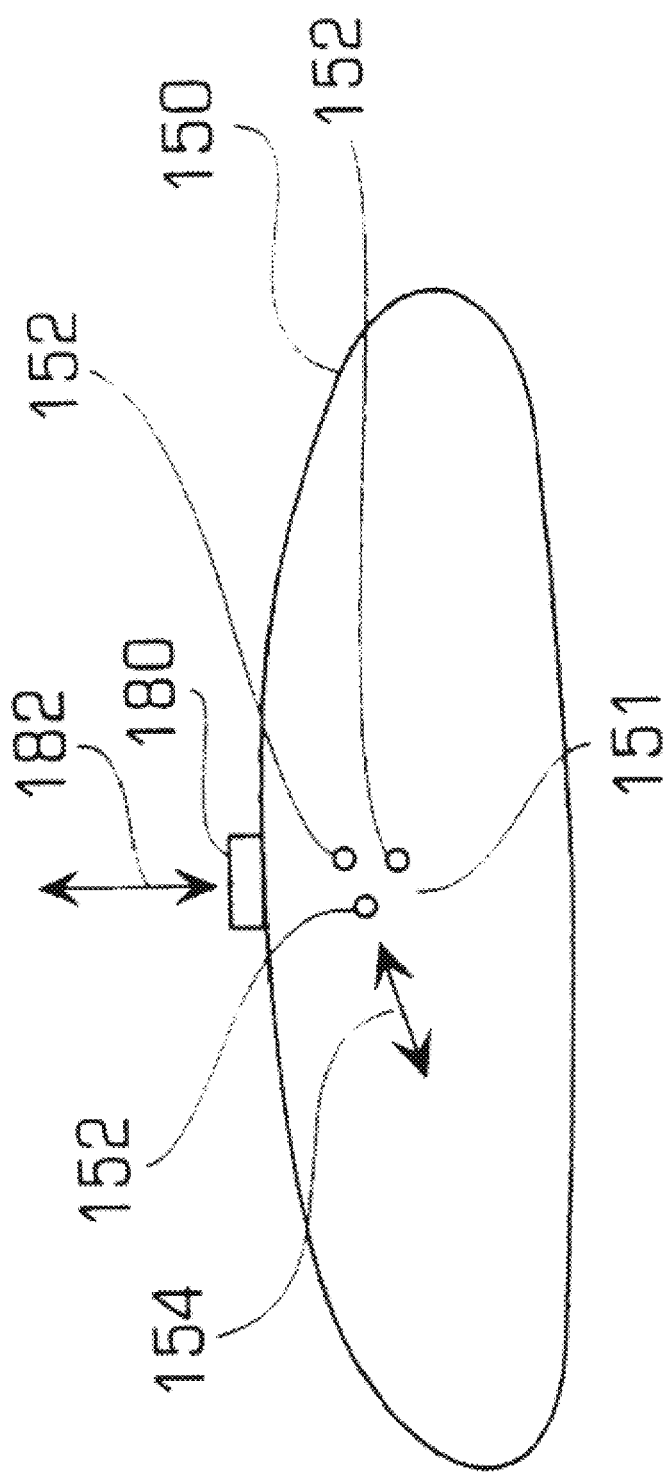
FIG. 3 is a diagram illustrating the internal markers in combination with an external marker to track the motion of the target region, according to embodiments.

FIG. 3 is a diagram illustrating a target (e.g., tumor) 151 within a patient's body 150 having internal markers 152 in combination with one or more external markers 180 attached to the skin of the patient. The one or more external markers 180 that are attached to the skin of the patient permit the motion 182,154 of the abdomen or chest wall to be determined. In the example of the breathing of a patient, the external marker may track the external motion as the patient inhales and exhales. The external markers 180 may be automatically tracked via an external detection device with a number of optical methods, such as infrared or visible light, and the position of the external marker may be determined more than 60 times per second. The external markers may also be attached to a belt, a flexible ring or a vest which fits around the waist of the patient.

In one embodiment, if only external markers are used to compensate for the motion of the patient, they may not accurately reflect the internal motion of the target organ since the target organ may move a small amount while the external marker may move a larger amount and vice versa. Furthermore, the primary axis of motion of an external marker is not necessarily the same as the primary axis of the internal target's motion. For example, a lung target may have a primary axis of motion in the patient inferior/superior direction, while an external chest marker may have a primary axis of motion in the anterior/posterior direction. The external markers alone may not be sufficiently precise to compensate for the motion of the patient. The combination of the internal markers and the external markers may be used to accurately track the motion of the target organ. The periodic X-ray imaging (e.g., via an internal detection device) of the internal markers may be correlated with the continuous optical tracking of the external markers (via an external tracking device) to provide accurate tracking of the motion of the target organ. In order to correlate the motion of the internal and external markers, the relationship between the positions of the internal and external markers may be determined, which may occur at the start of the treatment process and will be described below with reference to FIG. 4A-4D. It should be noted that in one embodiment, the Synchrony® respiratory tracking system may be used. Alternatively, other types of tracking systems may be used.

Figure 4A:
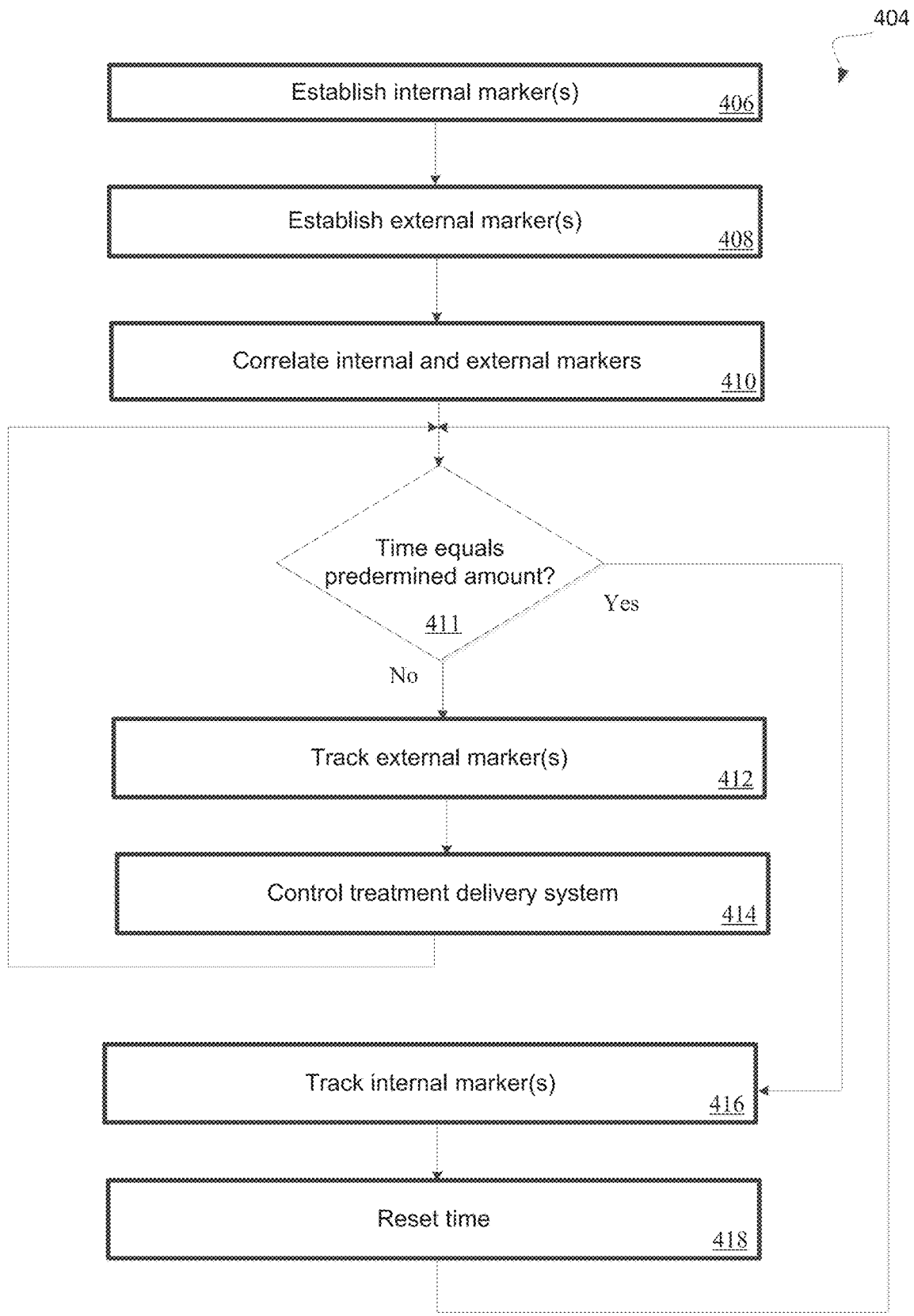
FIG. 4A is a flowchart illustrating a method for compensating for breathing and other motion in a treatment system, according to embodiments.

FIG. 4A is a flowchart illustrating a method 404 for compensating for changes in the position of a target (e.g., tumor) within a patient for breathing and/or other motion of the patient during radiation treatment delivery. In general, the method 404 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 404 may be performed by processing logic of the radiation treatment system 1200 of FIG. 1.

In one embodiment, the first few operations in the method may be performed at a time prior to the actual treatment of the patient. In particular, a surgeon may insert (e.g., establish) a set of internal markers (e.g., fiducials) in the proximity of or within the target organ during a short surgical procedure in block 406 and then, just prior to treatment, the surgeon may attach (e.g., establish) a set of external markers to the chest or abdominal wall of the patient near the target organ in block 408. In one embodiment, the external marks may be optical markers in an optical-based system. In another embodiment, other markers may be used. In some embodiments, the target (e.g., a fiducial, soft tissue, bone, etc.) may be tracked without the set of internal markers being inserted. Next, a processor, such as processor 602 of FIG. 8, of the radiation treatment device that receives positional information of the internal and external markers correlates the position of the internal markers and the external markers in block 410 just prior to starting the treatment of the patient. The method for correlating the internal markers with the external markers is described below. Once the positions of the internal and external markers have been correlated, the treatment of the patient may begin.

In one embodiment, the processing device of the radiation treatment system determines if the total elapsed time since the last time the internal markers were imaged is equal to a predetermined time period at block 411. The predetermined time period may be, for example, on the order of a few seconds. Alternatively, other time periods may be used. If the total elapsed time is equal to the predetermined time period, then the treatment beam is deactivated and the internal markers are imaged using, for example, x-ray imaging in block 416. In another embodiment, the treatment beam is not deactivated during the acquisition of new x-ray images. Next, the total elapsed time is reset to zero at block 418 and the method returns to block 411. Returning to block 411, if the total elapsed time is not equal to the predetermined time period, then the external markers are tracked in block 412 while the treatment beam is activated (e.g., the treatment delivery system is controlled) in block 414. The external markers may be tracked so that position data is provided to the processing device of the radiation treatment system, for example, sixty times per second. Alternatively, other time periods may be used. In some embodiments, the system may take x-ray images when the rotating gantry reaches predetermined angles. For example, an x-ray image may be taken every time the gantry passes 0 degrees and 90 degrees on each rotation. In other embodiments, a combination of time periods and angles may be used. The processing device may then correlate the position of the external markers with the internal markers and generate positional data about any change in the position of the target organ. Thus, between the periodic imaging of the internal markers, the position of the external markers is used to track the position of the target.

When movement of the target is detected, the radiation treatment system may compensate for the movement to control the radiation treatment delivery in a number of different ways. For example, the treatment system may move the LINAC and/or move the patient treatment couch to control the direction of the treatment beam relative to the target. The treatment system may turn the radiation treatment beam on or off to be coincident with the target. The treatment system may also shape or collimate the radiation treatment beam, modify the beam energy, or otherwise change the characteristics of the radiation treatment beam.

Embodiments of the present disclosure enable tracking the 3D position of the target inside the patient using data from two or more flat-panel X-ray images acquired at different times. The correlation between the moving internal 3D target position and the externally detected motion (e.g., breathing) amplitude is modeled using data acquired from multiple individual flat-panel X-ray images, all acquired at different times. Various mathematical approaches to sequential monoscopic tracking (SMT) may be used, two of which are discussed below. However, the present disclosure is not limited to only the two approaches discussed below. In alternative embodiments, other mathematical approaches may be used.

In one embodiment, the mathematical approach can be visualized as projecting lines from the X-ray source, through the (to be determined) target position model, onto the panel, and using linear algebra to solve for a target position model that minimizes the sum-of-least-squares difference between the projected model positions and the actual positions detected in 2-D on the panel (hereinafter referred to as "projecting lines approach"). The model can be a single static tumor position (for quasi-static tracking), or can be a function of breathing amplitude (for respiratory tracking).

The projecting lines mathematical approach is described below for (1) a helical radiation treatment delivery system with non-static target motion modeling (e.g., due to respiration or cardiac motion), (2) a helical radiation treatment delivery system with quasi-static target motion modeling; and (3) a radiation treatment delivery system, having a target motion tracking system, with non-static target motion modeling. However, the present disclosure is not limited to only the approaches discussed below. In alternative embodiments, other mathematical approaches may be used.

The mathematical approach discussed in this section may be in reference to a helical radiation delivery system such as the helical delivery system referenced herein. In cases (generally lung, liver, pancreas, breast, and renal treatments) where the target is expected to undergo significant respiratory motion, instead of using pairs of images to perform periodic correction, a model is built that allows real-time compensation for target motion. The first input to this model is a stream of 3D positions of external fiducials, or markers, on a vest worn by the patient. An example of external markers may be LEDs on the vest that are tracked, for example, at approximately 30 frames a second. The second input is periodic data from the imaging system, for example a single projection X-ray image. Specifically, each time an image is taken, the fiducials (fiducial treatments) or the target are localized in the X-ray image, with the help of a Digitally Reconstructed Radiograph (DRR) which uses the planning computerized tomography (CT) to simulate an X-ray projection at the desired angle. From the localization step, it is possible to deduce the line joining the X-ray source to the fiducial (or target) centroid. This line, together with the source position, is then the second input to the correlation model.

In the instance of a target being in the image, finding the line joining source to target is trivial: it is simply the line joining the source to the centroid of the target as identified on the detector plane. For the case involving multiple fiducials, however, taking the centroid of the fiducial constellation in the detector plane, and the line from this to the source, would give an incorrect result because the fiducials may be at different distances from the source.

One cannot derive exactly the fiducials' distances from the source in a single projection image, so instead we approximate the distances using the known 3D locations of the fiducials at nominal alignment. In some embodiments, each fiducial may be tracked individually and a 3D model corresponding to each tracked fiducial may be generated.

Writing $x_j$ as the positions of the fiducials at nominal alignment, $j=1\ldots N$, S as the position of the source, and $f_j$ as the 3D projections of the fiducials onto the detector plane (the 2D positions are determined by the localization algorithm, and a 3D projection is calculated by giving each fiducial an arbitrary "depth" corresponding to the detector), we estimate the 3D position $P_j$ of each fiducial as the closest point to $x_j$ on the line $S+\lambda(f_j-S)$. Specifically, we know that $$P_j = S + \lambda(f_j - S)$$

And also that $P_j$ lies on the perpendicular to the line from $x_j$, i.e., $$(x_j - P_j) \cdot (f_j - S) = 0$$

Solving these equations together gives $$\lambda = \frac{(x_j - S) \cdot (f_j - S)}{(f_j - S) \cdot (f_j - S)}$$

which allows us to estimate $P_j$, and thus take the mean value as the estimated centroid of the fiducial configuration. This position, in addition to the source, then defines the line which is sent to the modeler.

For embodiments in which the target does not experience significant respiratory and/or cardiac motion, it may be desirable to be able to perform periodic corrections for target translation, and to measure target rotation in order to ensure that it stays within acceptable bounds. To do this, pairs of images may be used; generally these will be the two most recent images taken with the gantry rotating, subject to some restrictions (e.g., the angle separation between the two images should be at least 30, and no more than 150 degrees).

Because the images taken with the kV snapshot imaging system on the gantry also share an inferior/superior direction, it is possible to extend the approach described above to account for angles that are not orthogonal, as with robotic based LINACs, as will be described in more detail below. However, the couch will be undergoing continual motion throughout treatment, and the effect of this motion on the projected fiducial positions varies according to the distance of each fiducial from the X-ray source. The extension of the robotic based LINAC approach to take account of this couch motion is non-trivial, and hence an alternate method is suggested.

For example, in a general case where there are N images (N would be equal to 2 if the workflow suggested above were used), and the camera projection matrix is allowed to vary between the images. In reality, unless flexion of the gantry causes significant change in the camera parameters, it can be assumed that the projection matrix remains constant.

The standard pinhole camera projection model can be represented by a projection matrix P where $$\begin{pmatrix} I_x \\ I_y \\ 1 \end{pmatrix} = \begin{pmatrix} fk_u & 0 & u_0 & 0 \\ 0 & -fk_v & v_0 & 0 \\ 0 & 0 & 1 & 0 \end{pmatrix} \begin{pmatrix} x_F \\ y_F \\ z_F \\ 1 \end{pmatrix} = P \begin{pmatrix} x_F \\ y_F \\ z_F \\ 1 \end{pmatrix}$$

F is the 3D coordinate system of the camera, f is the focal length (e.g., the distance between the X-ray source and the intersection of the source-detector axis with the center of the detector), $k_u$ and $k_v$ are the inverses of the pixel dimensions along the x and y image axes, $u_0$ and $v_0$ are the image coordinates of the intersections of the optical axis with the imaging plane, $\{x_F, y_F, z_F\}$ is the three dimensional position in the camera coordinate system of the object being projected, and $\{(I_{jx}, I_{jy})\}$ is the 2D image coordinate of the object as it appears in the projection (the X-ray image, in this case).

Before performing projections, the position of the object may be rendered from the imaging coordinate system into the camera coordinate system. This can be accomplished by a rigid transformation that we will label $R_j$, with the j suffix denoting the transformation from the imaging coordinate system to the camera coordinates for image j. Then, labeling the projection matrix for image j as $P_j$, we have $$I_j = P_j R_j (x_j + c_j)$$

where $c_j = \{c_{jx}, c_{jy}, c_{jz}\}^T$ is the vector representing couch offset at image j, $x = \{x\ y\ z\}^T$ is the position of the object in the imaging coordinate system, and $I_j = \{I_{jx}, I_{jy}\}^T$ is the 2D coordinate of the projection of the object on the imaging plane. Writing $T_j$ as the 3-by-4 matrix $P_j R_j$, in homogeneous coordinates $$I_{jx} = \frac{T_j^{11}(x + c_{jx}) + T_j^{12}(y + c_{jy}) + T_j^{13}(z + c_{jz}) + T_j^{14}}{T_j^{31}(x + c_{jx}) + T_j^{32}(y + c_{jy}) + T_j^{33}(z + c_{jz}) + T_j^{34}}$$

and $$I_{jy} = \frac{T_j^{21}(x + c_{jx}) + T_j^{22}(y + c_{jy}) + T_j^{23}(z + c_{jz}) + T_j^{24}}{T_j^{31}(x + c_{jx}) + T_j^{32}(y + c_{jy}) + T_j^{33}(z + c_{jz}) + T_j^{34}}$$

which can be rearranged into $$\begin{pmatrix} T_j^{31} I_{jx} - T_j^{11} & T_j^{32} I_{jx} - T_j^{12} & T_j^{33} I_{jx} - T_j^{13} \\ T_j^{31} I_{jy} - T_j^{21} & T_j^{32} I_{jy} - T_j^{22} & T_j^{33} I_{jy} - T_j^{23} \end{pmatrix} \begin{pmatrix} x \\ y \\ z \end{pmatrix} =$$

-continued $$\begin{pmatrix} T_j^{14} + c_{jx}(T_j^{11} - T_j^{31}I_{jx}) + c_{jy}(T_j^{12} - T_j^{32}I_{jx}) + c_{jz}(T_j^{13} - T_j^{33}I_{jx}) - T_j^{34}I_{jx} \\ T_j^{24} + c_{jx}(T_j^{21} - T_j^{31}I_{jy}) + c_{jy}(T_j^{22} - T_j^{32}I_{jy}) + c_{jz}(T_j^{23} - T_j^{33}I_{jy}) - T_j^{34}I_{jy} \end{pmatrix}$$

In general then, for N views, the equation is $$\begin{pmatrix} T_1^{31}I_{1x} - T_1^{11} & T_1^{32}I_{1x} - T_1^{12} & T_1^{33}I_{1x} - T_1^{13} \\ T_1^{31}I_{1y} - T_1^{21} & T_1^{32}I_{1y} - T_1^{22} & T_1^{33}I_{1y} - T_1^{23} \\ \vdots & \vdots & \vdots \\ T_N^{31}I_{Nx} - T_N^{11} & T_N^{32}I_{Nx} - T_N^{12} & T_N^{33}I_{Nx} - T_N^{13} \\ T_N^{31}I_{Ny} - T_N^{21} & T_N^{32}I_{Ny} - T_N^{22} & T_N^{33}I_{Ny} - T_N^{23} \end{pmatrix} \begin{pmatrix} x \\ y \\ z \end{pmatrix} =$$

$$\begin{pmatrix} T_1^{14} + c_{1x}(T_1^{11} - T_1^{31}I_{1x}) + c_{1y}(T_1^{12} - T_1^{32}I_{1x}) + c_{1z}(T_1^{13} - T_1^{33}I_{1x}) - T_1^{34}I_{1x} \\ T_1^{24} + c_{1x}(T_1^{21} - T_1^{31}I_{1y}) + c_{1y}(T_1^{22} - T_1^{32}I_{1y}) + c_{1z}(T_1^{23} - T_1^{33}I_{1y}) - T_1^{34}I_{1y} \\ \vdots \\ T_N^{14} + c_{Nx}(T_N^{11} - T_N^{31}I_{Nx}) + c_{Ny}(T_N^{12} - T_N^{32}I_{Nx}) + c_{Nz}(T_N^{13} - T_N^{33}I_{Nx}) - T_N^{34}I_{Nx} \\ T_N^{24} + c_{Nx}(T_N^{21} - T_N^{31}I_{Ny}) + c_{Ny}(T_N^{22} - T_N^{32}I_{Ny}) + c_{Nz}(T_N^{23} - T_N^{33}I_{Ny}) - T_N^{34}I_{Ny} \end{pmatrix}$$

As long as N>=2, the system is overdetermined, and the solution for x can be found by means of a standard matrix minimization method: find X to minimize $\|AX-B\|^2$, with the general solution $X=(A^TA)^{-1}A^TB$.

In one embodiment, this establishes a framework by which the estimated three dimensional position of each fiducial marker can be found by means of its projected locations in multiple X-ray images. It remains to use these fiducial marker positions to estimate the 6D corrections (translations and three roll angles) necessary to map from the nominal alignment position to the current target position.

In one embodiment, this is may be a point-based registration problem. There may be closed form solutions to finding the rigid transformation that maps one set of points to another corresponding set, such that the sum of squared distances between the points is minimized. Writing X as the set of fiducial positions in image coordinates, and Y as the corresponding positions at nominal alignment, the translation component is simply $\overline{X}-\overline{Y}$, e.g., the translation that maps the centroid of Y to the centroid of X. Writing $\tilde{X}$ and $\tilde{Y}$ as the two 3×N matrices of fiducial coordinates each with respect to their own centroid, and using Schönemann's solution and notation, the orthogonal matrix R minimizing $\|R\tilde{Y}-\tilde{X}\|^2$ is $R=UV^T$, where $\tilde{X}\tilde{Y}^T=UAV^T$ is the Singular Value Decomposition of $\tilde{X}\tilde{Y}^T$. It should be noted that both Horn's and Schönemann's solutions solve for an orthogonal matrix, which includes both rotations and reflections. A modification that allows the optimal rotation to be found may provide: in the case that the above solutions yield a reflection (i.e., det(R)=−1), the optimal rotation may be found by taking $R=USV^T$, where in the three dimensional case $$S = \begin{pmatrix} 1 & 0 & 0 \\ 0 & 1 & 0 \\ 0 & 0 & -1 \end{pmatrix}.$$

To derive the yaw, pitch and roll rotation angles y, p, and r the following convention may be used: we assume the x axis corresponds to the patient inferior-superior axis (and hence the axis about which the gantry rotates), the y axis corresponds to the patient left-right axis, and the z axis to the patient anterior-posterior axis. Further, we assume that the angles are applied in order yaw, pitch, and roll. Writing sy, cy, sp, cp, sr, cr as the sines and cosines of the angles, the rotation matrix comes out as $$\begin{pmatrix} cp\ cy & -cp\ sy & sp \\ cr\ sy + sr\ sp\ cy & cr\ cy - sr\ sp\ sy & -sr\ cp \\ sr\ sy - cr\ sp\ cy & sr\ cy + cr\ sp\ sy & cr\ cp \end{pmatrix}$$

This allows us to derive the values of the angles, which are $$y = \tan^{-1}(-R^{12}/R^{11})$$
$$p = \tan^{-1}\left(R^{13}/\sqrt{(R^{33})^2 + (R^{33})^2}\right)$$
$$r = \tan^{-1}(-R^{23}/R^{33})$$

In the another embodiment, the imaging isocenter may be designated as the origin of the image coordinate system. It may be assumed that the geometry of the imaging system is well characterized, so the positions $S_A$ and $S_B$ of the two X-ray sources in the imaging system are known, and the position and orientation of the X-ray detectors are known. Because the pixel size of the X-ray detectors is known, any detected fiducial position can be related to a coordinate in the imaging coordinate system lying on the detector surface.

We write as $\{F_{A1}, F_{A2}, \ldots, F_{AN}\}$ and $\{F_{B1}, F_{B2}, \ldots, F_{BN}\}$ these coordinates representing the projection of the fiducials onto the surfaces of detectors A and B, respectively. Then the true position of fiducial i can be written as lying on two lines defined by:

$$S_A + \lambda_{Ai}(F_{Ai} - S_A)$$

and $$S_B + \lambda_{Bi}(F_{Bi} - S_B)$$

where $\lambda_{Ai}$ and $\lambda_{Bi}$ are scalar parameters defining position along the line.

Ideally, the two lines would intersect, but because of uncertainty of fiducial localization and the calibration of the imaging system, typically the two lines do not exactly coincide, so a method must be found to estimate the fiducial position using the lines. Because the inferior/superior direction is shared between the two imaging planes, reconciling the two projections is as simple as taking the inferior/superior projected fiducial position in both planes to be the mean of the values from the two planes. With both projections having the same inferior/superior position, it becomes a simple back projection problem to find the 3D location that represents the intersection of the two modified fiducial projections.

In an alternative embodiment, the mathematical approach may be visualized as fuzzy cones projected from the source to the panel, rather than lines. The cones represent an uncertainty in the actual positions detected in 2-D by the panel. This uncertainty can be due to error in the 2-D detection (e.g., physical limitations like pixel size, imaging processing limitations, etc.). Uncertainty can also be due to patient motion between the times when images are acquired. Advantages of this approach in some embodiments may include: tunable parameters that represent the physical and algorithmic uncertainties of the system; tunable parameters that represent expected quasi-static patient motion or rate of deviation from an existing external/internal marker motion model (the aging parameter—i.e., the expected standard deviation of a measurement increases as the images age. Older images are effectively given less weight; and a statistical confidence metric defined as the likelihood of a given model explaining the measured data given the various tunable uncertainty parameters.

Rather than correlating breathing amplitudes with 3-D positions derived from stereoscopic image pairs, embodiments of the present disclosure build correlation directly between the breathing amplitude and the 2-D positions detected in sequentially acquired flat-panel images.

An internal-external correlation model can be implemented using many different functions, below are a few examples:

A linear function: $\bar{a}x+\bar{b}$, where x is the breathing amplitude and $\bar{a}$ and $\bar{b}$ are 3-D vectors The 5-D model (A linear function of both amplitude and its first derivative):

$$\overline{a}x = \overline{b}\frac{dx}{dt} + \overline{c}$$

A higher order polynomial model:

$$\sum_{i=1}^{N} \overline{c_i} x^i$$

Separate functions for inhalation and exhalation phases of breathing.

Each of these functions is made up of a number of parameters. For example, a linear model has 6 parameters that make up its two 3-D vectors. The 5-D model has 9 parameters, making up its three 3-D vectors.

Generating an internal-external correlation model is a matter of selecting the model type, and then determining values for all the model's parameters to best fit the observed data. With simultaneous pairs of images to give us 3-D measured target positions, this can be described mathematically as follows:

Let $\vec{p}_1, \vec{p}_2, \ldots \vec{p}_m$ be 3-D target locations measured at amplitudes $x_1, x_2, \ldots x_m$ respectively.

Let M(x) be a model function, with n parameters $c_1, c_2, \ldots c_n$.

Then optimize the model parameters to minimize the sum-of-square difference between the modeled 3-D positions and the measured 3-D positions:

$$\min_{c_1, c_2, \ldots, c_n} \Sigma_{i=1}^{m}(M(x_i)-\overline{p_i})^2$$

The above describes internal-external model building when the measured 3-D target locations are known. In embodiments of the present disclosure, an internal-external correlation model is built with only 2-D target locations detected in one flat-panel image at a time. The model generation involves an additional production of 3D model positions to 2D positions on the flat panel detector.

Let $\vec{q}_1, \vec{q}_2, \ldots \vec{q}_m$ be 2-D target locations on the flat-panel, measured at amplitudes
$x_1, x_2, \ldots x_m$ respectively.

Let M(x) be a model function, with n parameters $c_1, c_2, \ldots c_n$.

Let $Q_i(\vec{p})$ be a set of functions that project 3-D points in space onto the 2-D flat-panel, for the radiation source position and flat-panel position corresponding to each of the m measured amplitudes.

Then optimize the model parameters to minimize the sum-of-square difference between the modeled positions projected to 2-D and the measured 2-D positions on the flat-panel: $\min_{c_1, c_2, \ldots, c_n} \Sigma_{i=1}^{m}(M(x_i)-\overline{q_i})^2$ In one embodiment, this is the formula utilized to build a sequential monoscopic correlation model. In alternative embodiments, additional embellishments may be used to make the algorithm more robust and to detect tracking errors. In one embodiment, errors in model building are detected since sequential monoscopic modeling cannot rely on shared mutual information found in simultaneous image pairs. Simultaneous image pairs have one axis in common, so a discrepancy in the tracking results along that axis indicate some degree of tracking error To detect tracking errors in sequential monoscopic modeling, one can instead provide an estimate of the expected 2-D tracking error and 3-D patient modeling error, and then compute statistical confidence metrics for our model.

Let σ be the expected error between projected 2-D locations in the model and measured 2-D locations on the flat-panel.

Change the optimization equation to be $$\min_{c_1, c_2, \ldots, c_n} \sum_{i=1}^{m} \frac{(Q_i(M(x_i))-\vec{q}_i)^2}{\sigma^2}$$

The standard deviation between the projected model and measured points is then $$\sqrt{\frac{1}{m}\sum_{i=1}^{m} \frac{(Q_i(M(x_i))-\vec{q}_i)^2}{\sigma^2}}$$

This standard deviation between the model and measured data can be used to test whether this model is a good fit for the data.

The model building may be made more robust to changes over time by adjusting the expected standard deviation between projected model points and measured 2-D positions based on the age of the measurement:

Let $\sigma(\Delta t) = \sigma_1 + \sigma_7 \Delta t$, where $\sigma_1$ is the constant expected error in the 2-D position due to tracking accuracy and $\sigma_2$ is the rate at which the expected error increases over time—called the aging parameter.

Then optimize the model as $$\min_{c_1, c_2, \ldots, c_n} \sum_{i=1}^{m} \frac{(Q_i(M(x_i)) - \vec{q}_i)^2}{\sigma(t_m - t_i)^2}$$

This allows the model to use all available measurements, but more closely fit the newer measurements if the patient's breathing pattern has changed over time. Although embodiments of the present disclosure are described for use in modeling respiratory motion, alternate embodiments of the disclosed method and apparatus may be applied to modeling other types of motion such as cardiac motion. In another embodiment, the present disclosure may also be applied to quasi-static motion of a target.

In another embodiment, the least-squares minimization problem to derive a 3D motion model may be:

$$\min_{f} \sum_{i=1}^{n} \sum_{j=1}^{m} \|P_{g_i, c_i}(f(a_i, s_j)) - p_{i,j}\|^2$$

The motion model $f$ may be optimized such that the motion of fiducials inside the patient best matches the detected 2D fiducial locations in the X-ray images. The $p_{i,j}$ may be the 2D fiducial locations in the $i=1 \ldots n$ images, for $j=1 \ldots m$ fiducials. The motion model $f$ may be a function of the breathing amplitude $a_i$ at the time of image i acquisition and 3D fiducial position $s_j$ to a motion adjusted 3D position $s_j'$. The function $P_{g_i, c_i}$ projects the motion adjusted 3D position to its corresponding 2D position in the X-ray image, given gantry angle $g_i$ and couch position $c_i$ corresponding to image i.

In one embodiment, the system uses a fiducial detection algorithm to find the 2D fiducial locations ($p_{i,j}$), then uses a solver library to solve for the motion model in the equation above. Once an optimal model function has been calculated, the 3D location of the target can be predicted for any breathing amplitude in just a few milliseconds. In one example, let a be a breathing amplitude, and t be the 3D location of the target inside the patient without motion. Then the new 3-D target location t' is may be:

$$t' = f(a, t)$$

Motion models can take a variety of forms. For example, linear motion may be modeled as $f(a_i, s_j) = [x_1, y_1, z_1]a_i + [x_2, y_2, z_2] + s_j$. In this case, the minimization process may solve for six variables $(x_1, y_1, z_1, x_2, y_2, z_2)$ and so requires a minimum of three flat-panel images to construct the model. Additional images can be used to improve the robustness and statistical confidence of the model. More complex motion paths can be modeled using alternate motion model formulae. For example, the model function could be a higher-order polynomial (e.g., cubic) to handle non-linear target motion, or a dual-polynomial to handle hysteresis, where motion during inhalation differs from motion during exhalation.

In one embodiment, a motion model could also include rotation or even non-rigid spatial transforms. Models with more degrees of freedom require a greater minimum number of images to construct, and so require more additional images to reach the same level of robustness and statistical confidence as the linear model.

In practice, a patient's breathing pattern may not remain consistent over time. The system adapts to changes in breathing pattern by re-optimizing the model whenever a new image is acquired, taking about a second to process the image and update the model. In one embodiment, model adaptation is made more responsive to recent breathing changes by using only the n most recent images, and giving the more recent images more weight in the minimization objective function. In our formulation, weights are specified by increasing the expected error between the modeled versus predicted 2D locations, proportional to the age of the image.

In one example, let $\sigma$ represent the inherent accuracy of the 2D fiducial detection on the panel, e.g., resulting from the finite pixel size and accuracy of the geometric alignment of the kV imaging components. Let $\sigma'$ represent an expected rate of patient breathing pattern change over time, and $\Delta t_i = t_n - t_i$ be the time interval between the i-th image and the most recent (n-th) image, so $\Delta t_i \sigma'$ represents how much the breathing pattern in the i-th image is expected to deviate from the current model. The motion model minimization formula, with aging, is given below:

$$\min_{f} \sum_{i=1}^{n} \sum_{j=1}^{m} \left[ \frac{\|P_{g_i, c_i}(f(a_i, s_j)) - p_{i,j}\|}{\sigma + \Delta t_i \sigma'} \right]^2$$

With the inclusion of aging, sequential monoscopic imaging can effectively track non-respiratory motion as well as respiratory motion. One complication with non-respiratory motion may be that there is no continuous external signal, like breathing amplitude, to correlate with the periodic X-ray images. In one embodiment, the first indication the system has that motion has occurred is when the next X-ray image is acquired. Advantageously, to be more responsive to target motion, the system may prefer position information derived from the most recent image.

In one embodiment, to model non-respiratory motion using the model optimization framework above, we first define the motion model function to be independent of breathing amplitude—for example, the function $f(a_i, s_j) = [x, y, z] + s_j$ models static translation of the 3D target and fiducial positions. Second, we optimize the model using only the most recent few images, typically as few as only two images (e.g., n=2). Finally, the aging parameter ($\sigma'$) may be chose to be consistent with the speed non-respiratory targets are expected to move within the patient—e.g., prostates have been observed to move slowly due to bladder filling throughout treatment. Now the model minimization process can accurately calculate the 3D position of stationary targets, and efficiently handle moving targets by preferring the position information from more recent images.

In one embodiment, the model minimization framework also provides a way to verify the consistency of the model. With stereoscopic imaging, it is possible to compare the positions detected along the axis shared by the two simultaneous images to verify the tracking result. This may not be possible with sequential monoscopic imaging. Instead, we calculate model confidence as the probability that the optimized motion model is consistent with the 2D detected positions, given a priori expected detection accuracy ($\sigma$) and an image aging ($\sigma'$) parameter. This probability may be derived by calculating the area of the chi-squared distribution greater than the value of the optimized motion model. The degrees of freedom of the chi-squared distribution may be two times the number of 2D images times the number of fiducials (2mn). In one embodiment, the model confidence is shown mathematically in the equations below:

$$\chi^2_{opt} = \sum_{i=1}^{n} \sum_{j=1}^{m} \left[ \frac{\|P_{g_i, c_i}(f(a_i, s_j)) - p_{i,j}\|}{\sigma + \Delta t_i \sigma'} \right]^2$$

Model Confidence = $Pr[\chi^2(2mn) > \chi^2_{opt}]$

Figure 4B:
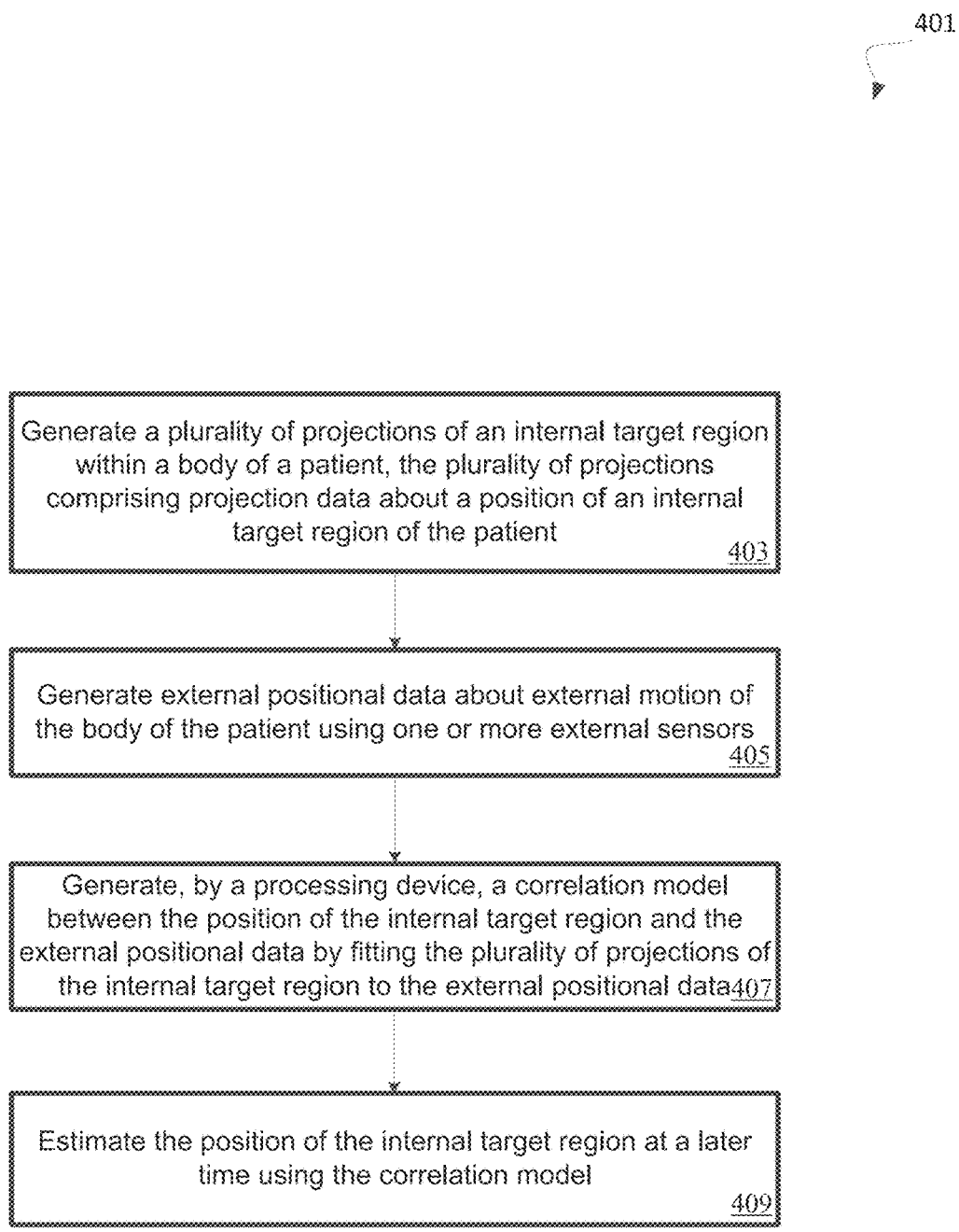
FIG. 4B is a first flowchart illustrating a method for sequential monoscopic tracking in a treatment system, according to embodiments.

FIG. 4B is a first flowchart illustrating a method for sequential monoscopic tracking in a treatment system, according to embodiments. In general, the method 401 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 401 may be performed by processing logic of the radiation treatment system 1200 of FIG. 1.

Beginning at block 403, processing logic may generate a plurality of projections of an internal target region within a body of a patient. In one embodiment, the plurality of projections include projection data about a position of an internal target region of the patient (e.g., via one or more internal detection devices). In one embodiment, the plurality of projections is sequentially acquired monoscopic projection images acquired using an imager (e.g., internal detection device) rotated on a gantry. In one embodiment, the plurality of projections is acquired at different points in time. The internal detection device may generate a single view of projection data at a time. The internal detection device may generate a plurality of sequential images, and generate a single projection based on the plurality of sequential images. In one embodiment, the projection data identifies internal motion of the patient's body, and the internal motion includes motion of the internal target region. In another embodiment, the projection data identifies internal motion of the patient's body, and the internal motion includes motion of one or more implanted fiducial markers.

At block 405, processing logic generates external positional data about external motion of the body of the patient using one or more external sensors (e.g., via one or more external detection devices). At block 407, processing logic generates, by a processing device, a correlation model between the projection data and the external positional data. In one embodiment, the correlation model may be generated by fitting the plurality of projections of the internal target region to the external positional data. In one embodiment, the correlation model identifies a best fit of an analytic function to the projection data identified in the plurality of projections and the corresponding external positional data. In one embodiment, processing logic generates the correlation model during acquisition of a CBCT scan (or some other type of scan). At block 409, processing logic estimates the position of the internal target region at a later time using the correlation model. Processing logic may, optionally, control the radiation treatment delivery system based on the correlation model.

In one embodiment, to control the radiation treatment delivery system based on the correlation model, the processing device is to direct a radiation treatment beam generated by a linear accelerator (LINAC) based on the correlation model. In another embodiment, to control the radiation treatment delivery system based on the correlation model, the processing device is to control a collimator of a linear accelerator (LINAC) based on the correlation model. In one embodiment, the collimator is a multi-leaf collimator and to control the collimator, the processing device is to move one or more leafs of the multi-leaf collimator. In another embodiment, to control the radiation treatment delivery system based on the correlation model, the processing device is to control a treatment couch. In another embodiment, to control the radiation treatment delivery system based on the correlation model, the processing device is to gate a radiation treatment beam generated by a linear accelerator (LINAC) based on the correlation model. In another embodiment, projection data corresponds to one or more fiducial markers located near the internal target region, and to generate the correlation model the processing device is to compute a deformation state of the internal target region based on relative positions of the one or more fiducial markers.

Figure 4C:
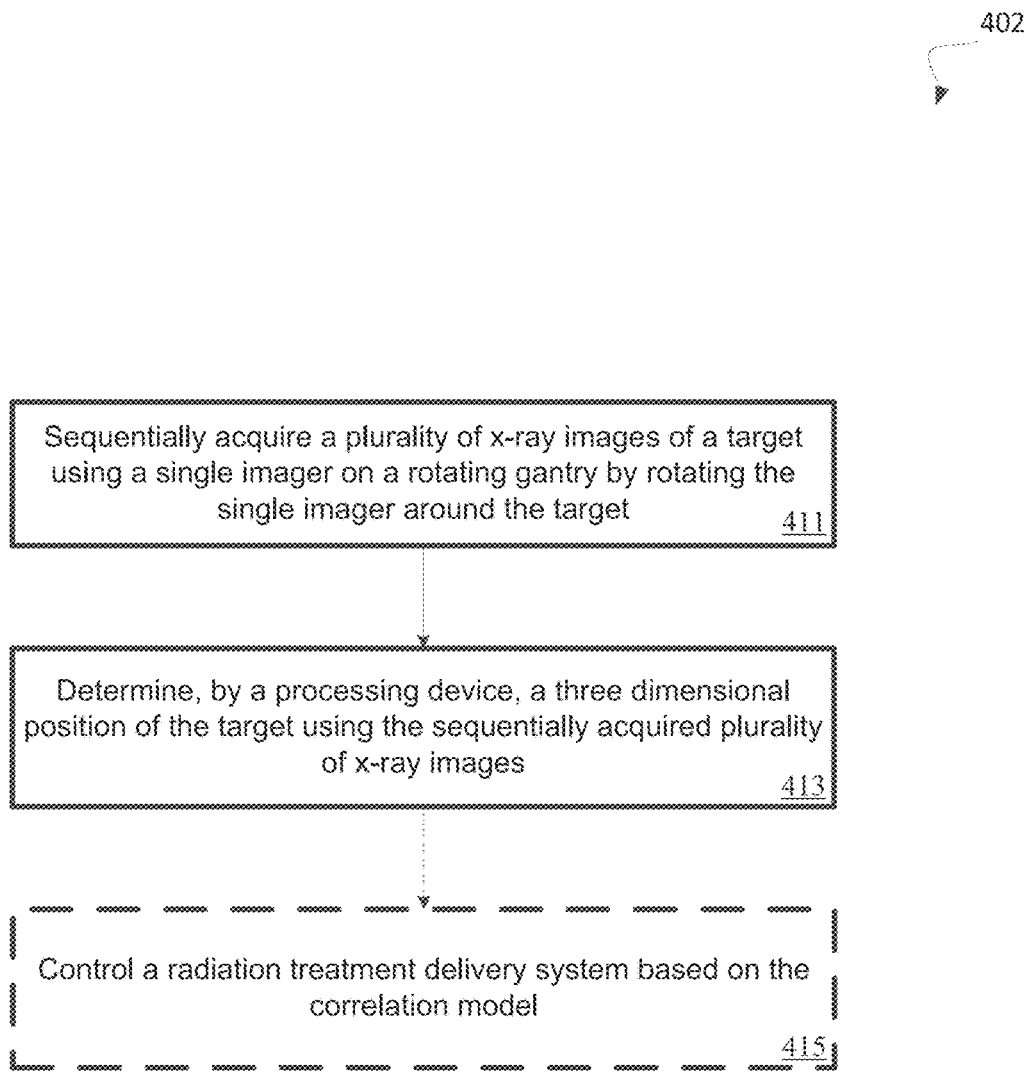
FIG. 4C is a second flowchart illustrating a method for sequential monoscopic tracking in a treatment system, according to embodiments.

FIG. 4C is a second flowchart illustrating a method for sequential monoscopic tracking in a treatment system, according to embodiments. In general, the method 402 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 402 may be performed by processing logic of the radiation treatment system 1200 of FIG. 1.

At block 411, processing logic sequentially acquires a plurality of x-ray images of a target using a single imager on a rotating gantry. In one embodiment, the plurality of x-ray images is acquired by rotating the single imager around the target. At block 413, processing logic determines, by a processing device, a three dimensional position of the target using the sequentially acquired plurality of x-ray images. At block 415, processing logic optionally controls a radiation treatment delivery system based on the correlation model.

Figure 4D:
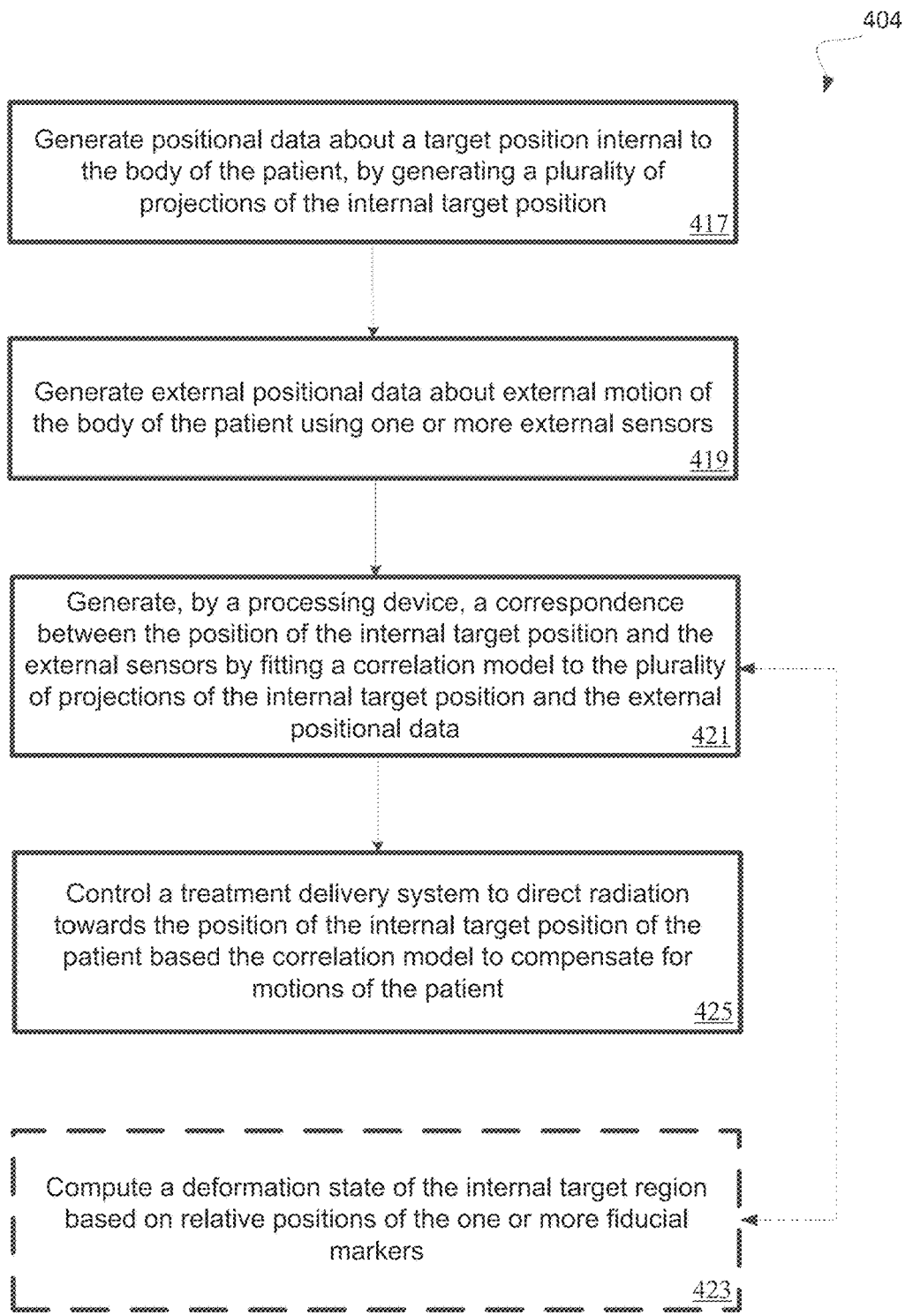
FIG. 4D is a third flowchart illustrating a method for sequential monoscopic tracking in a treatment system, according to embodiments.

FIG. 4D is a third flowchart illustrating a method for sequential monoscopic tracking in a treatment system, according to embodiments. In general, the method 404 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 404 may be performed by processing logic of the radiation treatment system 1200 of FIG. 1.

At block 417, processing logic generates positional data about a target position internal to the body of the patient. In one embodiment, processing logic generates the positional data by generating a plurality of projections of the internal target position. At block 419, processing logic generates external positional data about external motion of the body of the patient using one or more external sensors. In one embodiment, the external positional data is continuously generated, wherein "continuously" is used to mean that the external positional data is generated more frequently than "periodically" generated projections. For example, continuously generated external data could mean external position data generated at 30 Hz; while periodically generated projection data could be generated once every 30 seconds; or similarly discrepant time intervals, where "continuously" generated data is generated orders of magnitude more frequently than "periodically" generated data. At block 421, processing logic generates, by a processing device, a correspondence between the position of the internal target position and the external sensors by fitting a correlation model to the plurality of projections of the internal target position and the external positional data. Optionally, the internal positional data corresponds to one or more fiducial markers located near the internal target region and at block 423, processing logic computes a deformation state of the internal target region based on relative positions of the one or more fiducial markers, to generate the correlation model. At block 425, processing logic controls a treatment delivery system to direct radiation towards the position of the internal target position of the patient based the correlation model to compensate for motions of the patient.

Figure 5:
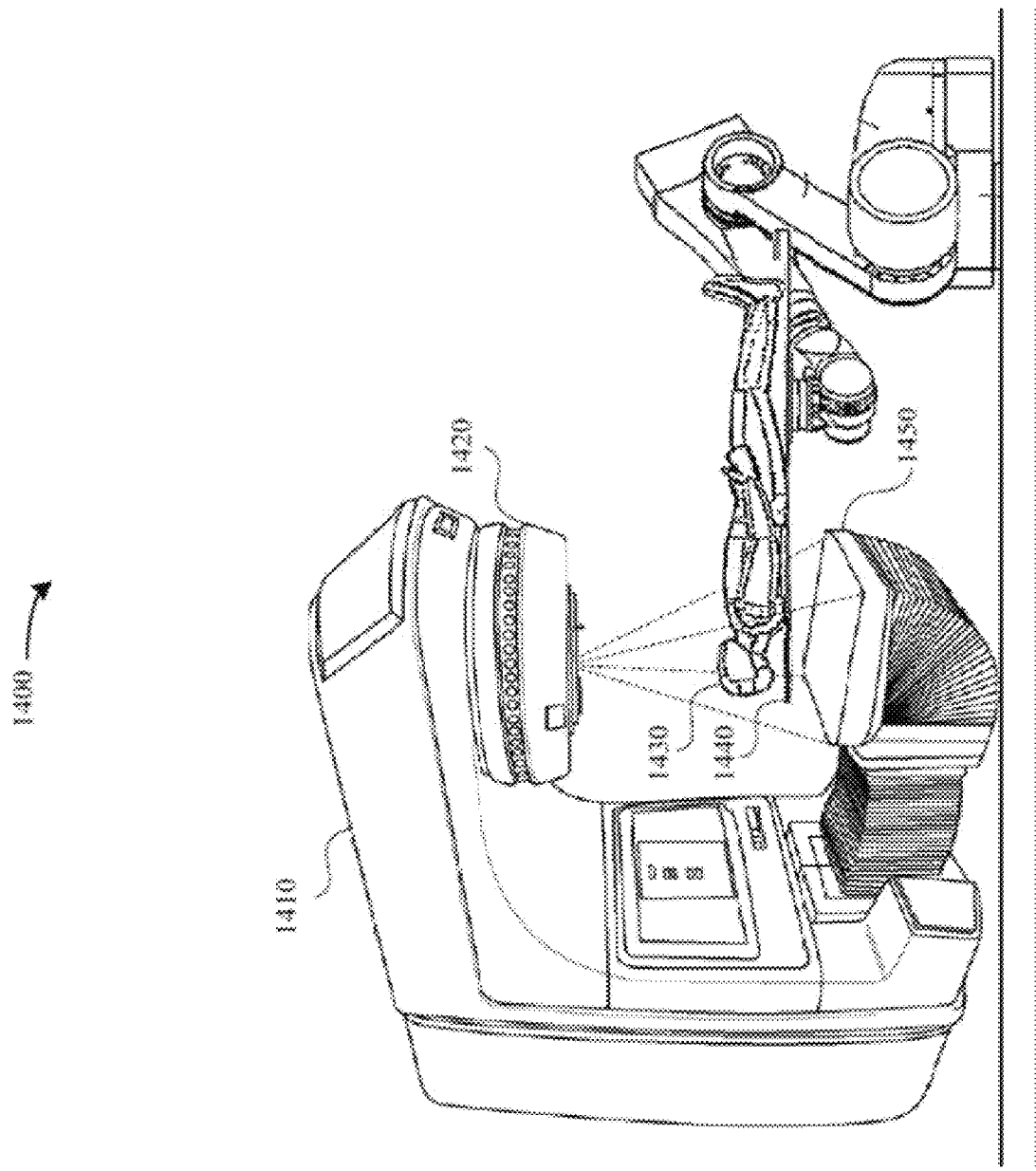
FIG. 5 illustrates a portal imaging radiation treatment system, in accordance with embodiments described herein.

Embodiments of the present disclosure may be implemented in a portal imaging system 1400 as shown in FIG. 5. In one embodiment, in the portal imaging system 1400 the beam energy of a LINAC may be adjusted during treatment and may allow the LINAC to be used for both x-ray imaging (e.g., generating the monoscopic images) and radiation treatment. In another embodiment, the system 1400 may include an onboard kV imaging system to generate x-ray images (e.g., monoscopic images) and a separate LINAC to generate the higher energy therapeutic radiation beams. The system 1400 includes a gantry 1410, a LINAC 1420 and a portal imaging detector 1450. The gantry 1410 may be rotated to an angle corresponding to a selected projection and used to acquire an x-ray image of a VOI of a patient 1430 on a treatment couch 1440. In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above.

Figure 6:
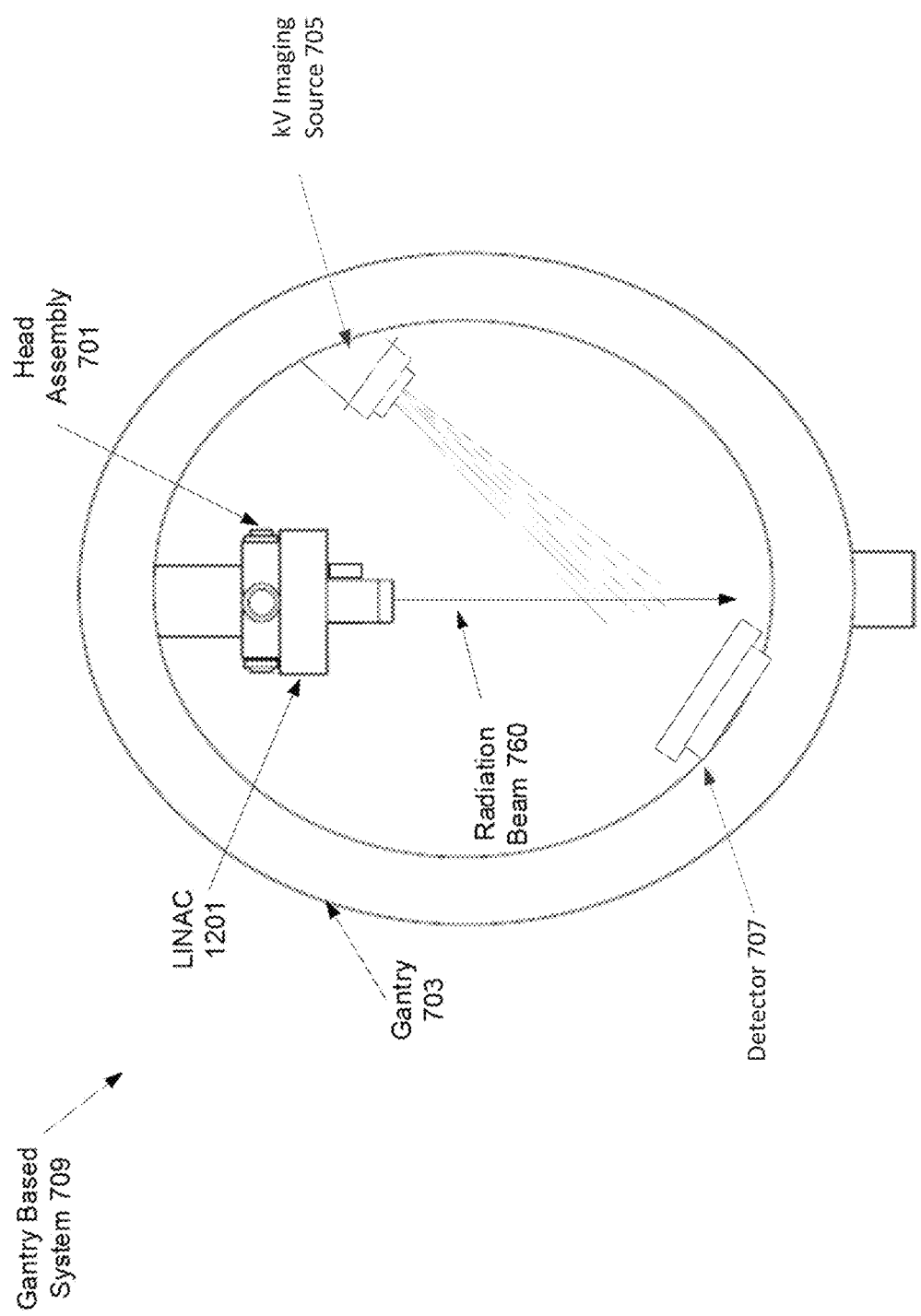
FIG. 6 illustrates a gantry based intensity modulated radiation treatment system, in accordance with embodiments described herein.

FIG. 6 illustrates a gantry based intensity modulated radiation treatment (IMRT) system 709, in accordance with implementations of the present disclosure. In gantry based system 709, a radiation source (e.g., a LINAC 1201) having a head assembly 701 is mounted on a gantry 703. In one embodiment, radiation beams 160 may be delivered from several positions on a circular plane of rotation (e.g., around an axis of rotation). In one embodiment, system 709 includes a treatment imaging system, which may include a kV imaging source 705 and an x-ray detector 707. The kV imaging source 705 may be used to generate x-ray images of a region of interest (ROI) of patient by directing a sequence of x-ray beams at the ROI which are incident on the x-ray detector 707 opposite the kV imaging source 705 to image the patient for setup and generate in-treatment images. The resulting system generates arbitrarily shaped radiation beams 760 that intersect each other at an isocenter to deliver a dose distribution to the target location. In one implementation, the gantry based system 700 may be a c-arm based system.

Figure 7:
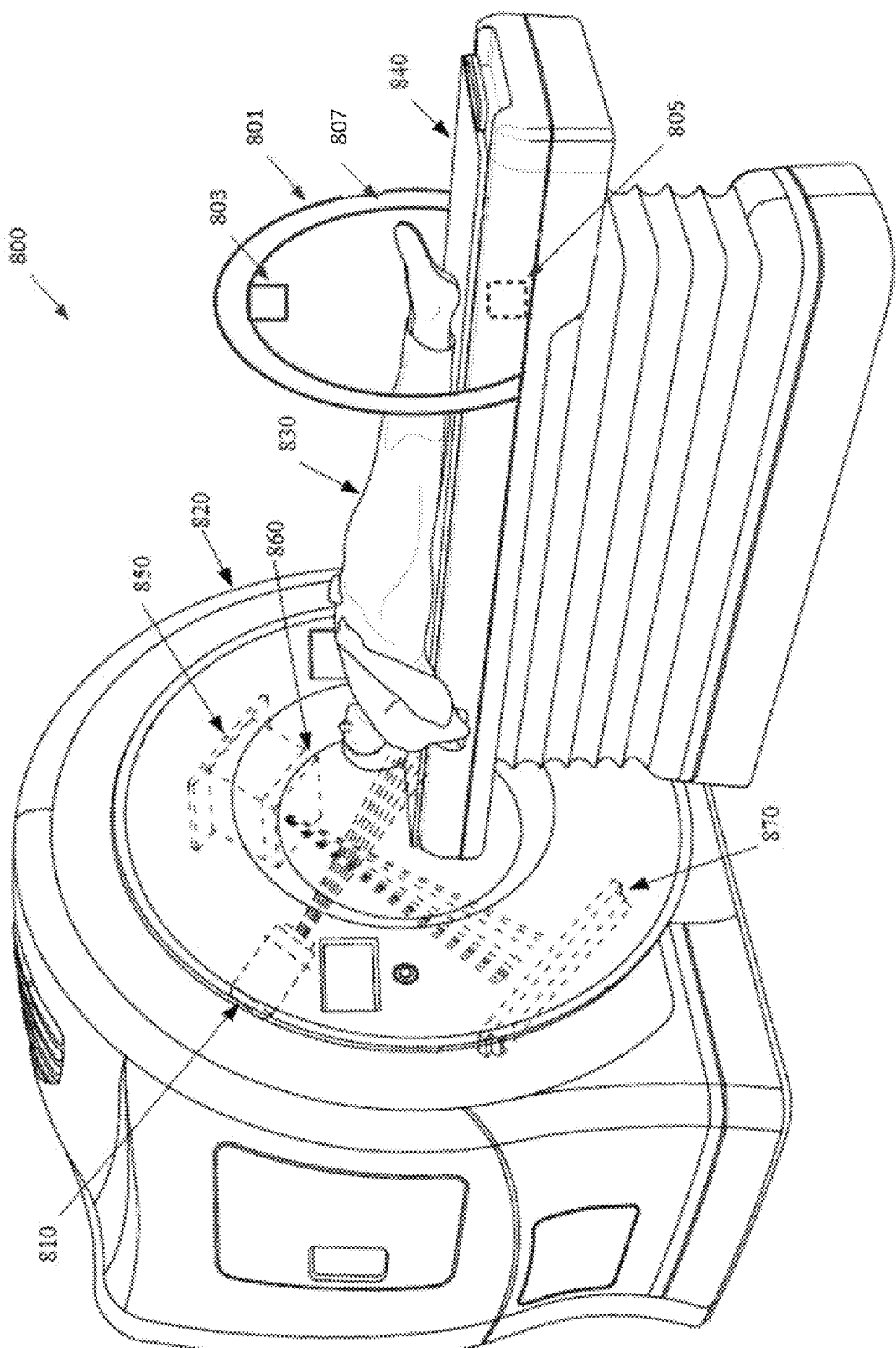
FIG. 7 illustrates a helical radiation delivery system, in accordance with embodiments described herein.

FIG. 7 illustrates a helical radiation delivery system 800 in accordance with embodiments of the present disclosure. The helical radiation delivery system 800 may include a linear accelerator (LINAC) 810 mounted to a ring gantry 820. The LINAC 810 may be used to generate a narrow intensity modulated pencil beam (i.e., treatment beam) by directing an electron beam towards an x-ray emitting target. The treatment beam may deliver radiation to a target region (i.e., a tumor). The ring gantry 820 generally has a toroidal shape in which the patient 830 extends through a bore of the ring/toroid and the LINAC 810 is mounted on the perimeter of the ring and rotates about the axis passing through the center to irradiate a target region with beams delivered from one or more angles around the patient. During treatment, the patient 830 may be simultaneously moved through the bore of the gantry on treatment couch 840.

The helical radiation delivery system 800 includes a treatment imaging system, which may include a kV imaging source 850 and an x-ray detector 870. The kV imaging source 850 may be used to generate x-ray images of a region of interest (ROI) of patient 830 by directing a sequence of x-ray beams at the ROI which are incident on the x-ray detector 870 opposite the kV imaging source 850 to image the patient 830 for setup and generate in-treatment images. The treatment imaging system may further include a collimator 860. In one embodiment, the collimator 860 may be a variable aperture collimator. In another embodiment, the collimator 860 may be a multi-leaf collimator (MLC). The MLC includes a housing that houses multiple leaves that are movable to adjust an aperture of the MLC to enable shaping of an imaging x-ray beam. In another embodiment, the variable aperture collimator 860 may be an iris collimator containing trapezoidal blocks that move along a frame in a manner similar to a camera iris to produce an aperture of variable size that enables shaping of the imaging x-ray beam. The kV imaging source 850 and the x-ray detector 870 may be mounted orthogonally relative to the LINAC 810 (e.g., separated by 90 degrees) on the ring gantry 820 and may be aligned to project an imaging x-ray beam at a target region and to illuminate an imaging plane of detector 870 after passing through the patient 130. In some embodiments, the LINAC 810 and/or the kV imaging source 850 may be mounted to a C-arm gantry in a cantilever-like manner, which rotates the LINAC 810 and kV imaging source 850 about the axis passing through the isocenter.

Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Helical radiation delivery system 800 includes also includes a secondary imaging system 801. Imaging system 801 is a CBCT imaging system, for example, the medPhoton ImagingRing System. Alternatively, other types of volumetric imaging systems may be used. The secondary imaging system 801 includes a rotatable gantry 807 (e.g., a ring) attached to an arm and rail system (not shown) that move the rotatable gantry 807 along one or more axes (e.g., along an axis that extends from a head to a foot of the treatment couch 840. An imaging source 803 and a detector 805 are mounted to the rotatable gantry 807. The rotatable gantry 807 may rotate 360 degrees about the axis that extends from the head to the foot of the treatment couch. Accordingly, the imaging source 803 and detector 805 may be positioned at numerous different angles. In one embodiment, the imaging source 803 is an x-ray source and the detector 805 is an x-ray detector. In one embodiment, the secondary imaging system 801 includes two rings that are separately rotatable. The imaging source 803 may be mounted to a first ring and the detector 805 may be mounted to a second ring.

Figure 8:
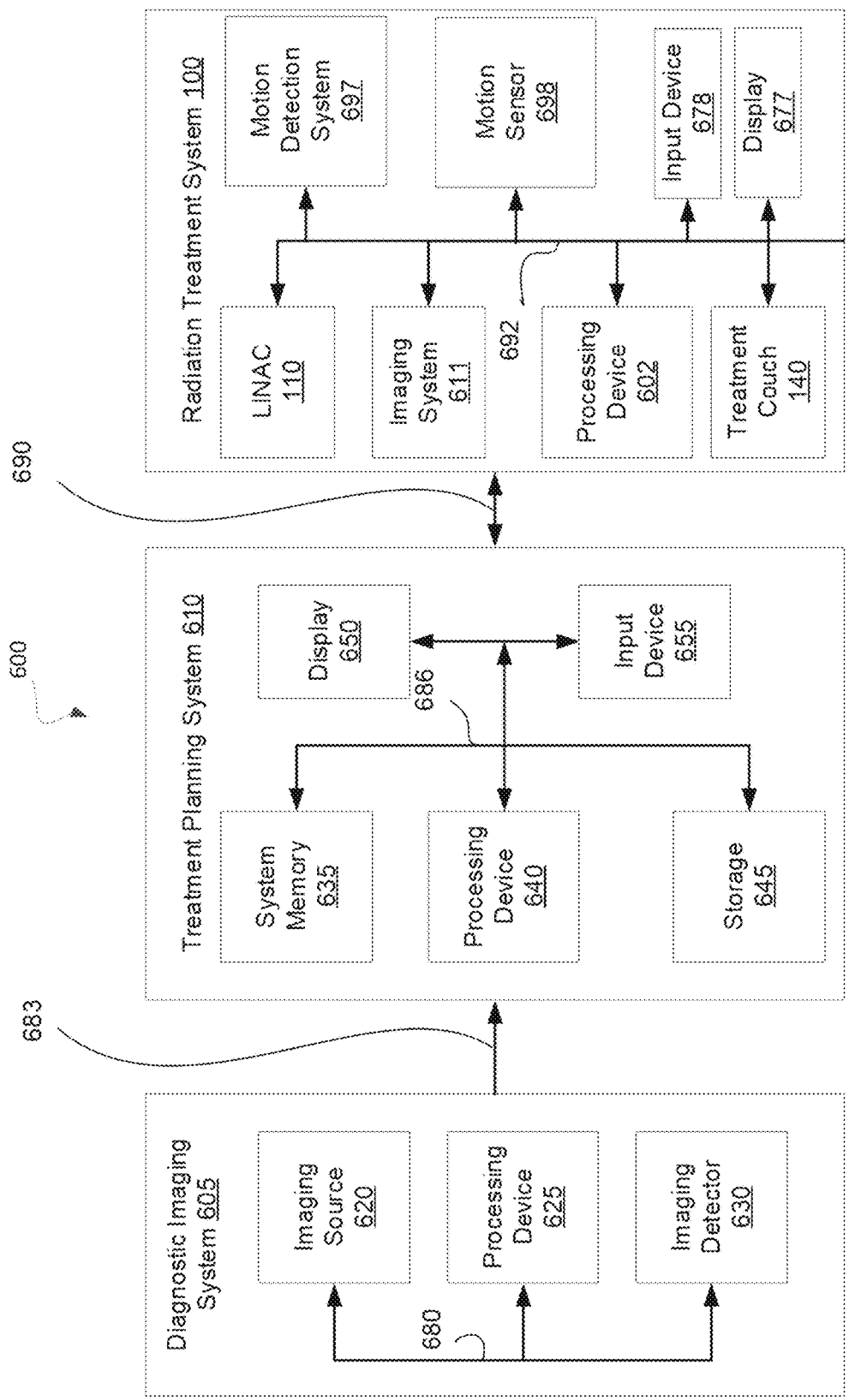
FIG. 8 illustrates examples of different systems that may be used in the generating of the performing of radiation treatment, in accordance with embodiments described herein.

FIG. 8 illustrates examples of different systems 600 within which a set of instructions, for causing the systems to perform any one or more of the methodologies discussed herein, may be executed. In alternative implementations, the machine may be connected (e.g., networked) to other machines in a local area network (LAN), an intranet, an extranet, and/or the Internet. Each of the systems may operate in the capacity of a server or a client machine in client-server network environment, as a peer machine in a peer-to-peer (or distributed) network environment, or as a server or a client machine in a cloud computing infrastructure or environment.

The example radiation treatment delivery system 100, which may represent treatment delivery systems 1200, 800, 709, or some other system, includes a processing device 602, a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), and a data storage device, which communicate with each other via a bus.

The systems are machines capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

FIG. 8 illustrates examples of different systems 600 within which a set of instructions, for causing the systems to perform any one or more of the methodologies discussed herein, may be executed. In alternative implementations, the machine may be connected (e.g., networked) to other machines in a local area network (LAN), an intranet, an extranet, and/or the Internet. Each of the systems may operate in the capacity of a server or a client machine in client-server network environment, as a peer machine in a peer-to-peer (or distributed) network environment, or as a server or a client machine in a cloud computing infrastructure or environment.

The example radiation treatment delivery system 100, which may represent treatment delivery systems 1200, 800, 709, or some other system, includes a processing device 602, a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), and a data storage device, which communicate with each other via a bus.

Processing device 602 represents one or more general-purpose processing devices such as a microprocessor, a central processing unit, or the like. Processing device may be the same or a different processing device as processing device 1230 and may also represent the processing device in treatment delivery workstation 150. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute instructions for performing the operations and steps discussed herein.

The computer system 600 may further include a network interface device to communicate over the network. The computer system 600 also may include a video display unit (e. g., a liquid crystal display (LCD) or a cathode ray tube (CRT)), an alphanumeric input device (e. g., a keyboard), a cursor control device (e. g., a mouse), a graphics processing unit, a signal generation device (e.g., a speaker), graphics processing unit, video processing unit, and audio processing unit.

The data storage device 618 may include a machine-readable storage medium 624 (also known as a computer-readable medium) on which is stored one or more sets of instructions or software 626 embodying any one or more of the methodologies or functions described herein. The instructions 626 may also reside, completely or at least partially, within the main memory 604 and/or within the processing device 602 during execution thereof by the computer system 600, the main memory 604 and the processing device 602 also constituting machine-readable storage media.

In one implementation, the instructions 626 include an x-ray motion component to implement functionality corresponding to the disclosure herein. While the machine-readable storage medium is shown in an example implementation to be a single medium; the term "machine-readable storage medium' should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

It will be apparent from the foregoing description that aspects of the present disclosure may be embodied, at least in part, in software. That is, the techniques may be carried out in a computer system or other data processing system in response to a processing device 625, 640, or 602 (see FIG. 8), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 602.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method, comprising:
generating a plurality of two dimensional projections of an internal target region within a body of a patient, the plurality of two dimensional projections comprising two dimensional projection data about a two dimensional position of an internal target region of the patient, wherein each of the plurality of two dimensional projections are generated sequentially at different points in time;
generating external positional data about external motion of the body of the patient using one or more external sensors;
generating, by a processing device, a correlation model between the external positional data and a three dimensional position of the internal target region by directly fitting, in two dimensions, the plurality of two dimensional projections of the internal target region, generated sequentially at different points in time, to the external positional data, wherein directly fitting the plurality of two dimensional projections of the internal target region to the external positional data comprises identifying a best fit of an analytic function with respect to the plurality of two dimensional projections and the external positional data, wherein the analytic function projects a three dimensional position into two dimensions; and
estimating the three dimensional position of the internal target region at a later time using the correlation model.

2. The method of claim 1, wherein the plurality of two dimensional projections is sequentially acquired monoscopic projection images acquired using an imager rotated on a gantry.

3. The method of claim 1, wherein the two dimensional projection data identifies internal motion of the patient's body, the internal motion comprising motion of the internal target region.

4. The method of claim 1, wherein the two dimensional projection data identifies internal motion of the patient's body, the internal motion comprising motion of one or more implanted fiducial markers.

5. The method of claim 1, the method further comprising: directing a radiation treatment beam generated by a linear accelerator (LINAC) based on the correlation model.

6. The method of claim 1 the method further comprising: controlling a collimator of a linear accelerator (LINAC) based on the correlation model.

7. The method of claim 6, wherein the collimator is a multi-leaf collimator and to control the collimator, the method comprising moving one or more leafs of the multi-leaf collimator.

8. The method of claim 1, the method further comprising: controlling a treatment couch.

9. The method of claim 1, the method further comprising: gating a radiation treatment beam generated by a linear accelerator (LINAC) based on the correlation model.

10. The method of claim 1, wherein the projection data corresponds to one or more fiducial markers located near the internal target region, wherein to generate the correlation model the method further comprising: computing a deformation state of the internal target region based on relative positions of the one or more fiducial markers.

11. A radiation treatment delivery apparatus, comprising:
a first detection device to generate two dimensional projection data about a target region internal to a body of a patient, wherein the two dimensional projection data comprises two dimensional projections generated sequentially at different points in time;
a second detection device to generate positional data about one or more sensors external to the body of the patient; and
a processing device to receive the two dimensional projection data about the internal target region and the positional data from the external sensors and generate a correspondence between the positional data and a three dimensional position of the internal target region by directly fitting the two dimensional projection data of the internal target region, generated sequentially at different points in time, to the external sensors to control the radiation treatment delivery apparatus based on the position data obtained from the external sensors to compensate for motions of the patient, wherein directly fitting the two dimensional projections of the internal target region to the external sensors comprises identifying a best fit of an analytic function with respect to the two dimensional projections and the external sensors, wherein the analytic function projects a three dimensional position into two dimensions.

12. The apparatus of claim 11, wherein the first detection device comprises a rotatable single imager.

13. The apparatus of claim 12, further comprising a linear accelerator (LINAC) comprising an onboard kilovoltage (kV) imager coupled to a gantry, wherein the first detection device is coupled to the gantry.

14. The apparatus of claim 11, wherein the first detection device is further to:
generate a plurality of sequential images; and
generate a single projection based on the plurality of sequential images.

15. The apparatus of claim 11, further comprising a linear accelerator (LINAC) coupled to a moveable stage, wherein the first detection device comprises a cone-beam CT (CBCT) imager coupled to a gantry.

16. The apparatus of claim 15, wherein the moveable stage is the gantry.

17. The apparatus of claim 15, wherein the moveable stage is separate from the gantry.

18. The apparatus of claim 15, wherein the correspondence between the positional data and three dimensional position of the internal target region is generated during acquisition of a CBCT scan.

19. The apparatus of claim 15, wherein the first detection device comprises a portal imager.

20. A non-transitory computer readable medium comprising instructions that, when executed by a processing device of a radiation treatment delivery system, cause the processing device to:
generate a plurality of two dimensional projections of an internal target region within a body of a patient, the plurality of two dimensional projections comprising two dimensional projection data about a two dimensional position of an internal target region of the patient, wherein each of the plurality of two dimensional projections are generated sequentially at different points in time;
generate external positional data about external motion of the body of the patient using one or more external sensors;
generate, by the processing device, a correlation model between the external positional data and a three dimensional position of the internal target region by directly fitting, in two dimensions, the plurality of two dimensional projections of the internal target region generated sequentially at different points in time to the external positional data, wherein directly fitting the plurality of two dimensional projections of the internal target region to the external positional data comprises identifying a best fit of an analytic function with respect to the plurality of two dimensional projections and the external positional data, wherein the analytic function projects a three dimensional position into two dimensions; and
estimate the three dimensional position of the internal target region at a later time using the correlation model.

21. The non-transitory computer readable medium of claim 20, wherein the plurality of projections is sequentially acquired monoscopic projection images acquired using an imager rotated on a gantry.

22. The non-transitory computer readable medium of claim 20, wherein the two dimensional projection data identifies internal motion of the patient's body, the internal motion comprising motion of the internal target region.

23. The non-transitory computer readable medium of claim 20, wherein the two dimensional projection data identifies internal motion of the patient's body, the internal motion comprising motion of one or more implanted fiducial markers.

24. A method, comprising:
sequentially acquiring a plurality of two dimensional x-ray images of a target using a single imager on a rotating gantry by rotating the single imager around the target, wherein each of the plurality of two dimensional x-ray images are acquired sequentially at different points in time; and
determining, by a processing device, a three dimensional position of the target directly using the sequentially acquired plurality of two dimensional x-ray images, wherein determining the three dimensional position of the target directly using the sequentially acquired plurality of two dimensional x-ray images comprises identifying a best fit of an analytic function with respect to the plurality of two dimensional x-ray images, wherein the analytic function projects a three dimensional position into two dimensions.

25. The method of claim 24, further comprising controlling a radiation treatment delivery system based on a correlation model.

26. A method, comprising:
generating two dimensional positional data about a two dimensional target position internal to a body of a patient, by generating a plurality of two dimensional projections of the two dimensional internal target position, wherein each of the plurality of two dimensional projections are generated sequentially at different points in time;
generating external positional data about external motion of the body of the patient using one or more external sensors, wherein the external positional data is generated more frequently than the plurality of two dimensional projections; and
generating, by a processing device, a correspondence between the external positional data and a three dimensional position of the target by directly fitting a correlation model to the plurality of two dimensional projections of the two dimensional internal target position, generated sequentially at different points in time, and the external positional data, wherein fitting the correlation model comprises identifying a best fit of an analytic function with respect to the plurality of projections and the external positional data, wherein the analytic function projects a three dimensional position into two dimensions; and controlling a treatment delivery system to direct radiation towards the three dimensional position of the internal target position of the patient based the correlation model to compensate for motions of the patient.

27. The method of claim 26, wherein the positional data corresponds to one or more fiducial markers located near the internal target position, wherein generating the correlation model comprises computing a deformation state of the internal target position based on relative positions of the one or more fiducial markers.

* * * * *